United States Patent
Lee et al.

(10) Patent No.: US 11,335,862 B2
(45) Date of Patent: May 17, 2022

(54) ORGANIC ELECTROLUMINESCENCE DEVICE AND POLYCYCLIC COMPOUND FOR ORGANIC ELECTROLUMINESCENCE DEVICE

(71) Applicant: Samsung Display Co., Ltd., Yongin-si (KR)

(72) Inventors: Jungsub Lee, Hwaseong-si (KR); Hyein Jeong, Suwon-si (KR); Hye Jeong Park, Hwaseong-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 286 days.

(21) Appl. No.: 16/575,109

(22) Filed: Sep. 18, 2019

(65) Prior Publication Data

US 2020/0185606 A1 Jun. 11, 2020

(30) Foreign Application Priority Data

Dec. 5, 2018 (KR) .......................... 10-2018-0155173

(51) Int. Cl.
*H01L 51/00* (2006.01)
*C07F 5/02* (2006.01)
(Continued)

(52) U.S. Cl.
CPC .......... *H01L 51/008* (2013.01); *C07D 495/06* (2013.01); *C07F 5/027* (2013.01);
(Continued)

(58) Field of Classification Search
CPC ............... H01L 51/008; H01L 51/0061; H01L 51/0071; H01L 51/0074; H01L 51/0072;
(Continued)

(56) References Cited

U.S. PATENT DOCUMENTS

| 9,947,876 B2 | 4/2018 | Kawamura et al. |
| 2016/0133854 A1* | 5/2016 | Heil ........................ C09K 11/06 252/301.16 |
| 2020/0411771 A1* | 12/2020 | Kim .................... H01L 51/0058 |

FOREIGN PATENT DOCUMENTS

| KR | 10-2011-0113297 A | 10/2011 |
| KR | 10-2011-0116635 A | 10/2011 |

(Continued)

*Primary Examiner* — Alexander C Kollias
(74) *Attorney, Agent, or Firm* — Lewis Roca Rothgerber Christie LLP

(57) ABSTRACT

An organic electroluminescence device according to an embodiment of the present disclosure includes a first electrode, a hole transport region, an emission layer, an electron transport region, and a second electrode, in which the emission layer includes a polycyclic compound represented by Formula 1, thereby achieving improved emission efficiency:

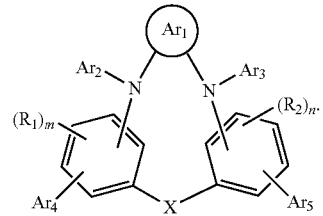

Formula 1

19 Claims, 2 Drawing Sheets

(51) Int. Cl.
  *C09K 11/06* (2006.01)
  *C07D 495/06* (2006.01)
  *H01L 51/50* (2006.01)

(52) U.S. Cl.
  CPC .......... *C09K 11/06* (2013.01); *H01L 51/0061* (2013.01); *C09K 2211/1018* (2013.01); *C09K 2211/1022* (2013.01); *H01L 51/0005* (2013.01); *H01L 51/0071* (2013.01); *H01L 51/5012* (2013.01); *H01L 51/5016* (2013.01)

(58) Field of Classification Search
  CPC .... H01L 51/0054; H01L 51/006; C07F 5/027; C07F 5/02; C09K 2211/1022; C09K 2211/1018; C07D 403/14; C07D 417/14; C07D 495/08; C07D 495/06; C07D 245/04; C07D 405/14; C07D 255/04
  See application file for complete search history.

(56) References Cited

FOREIGN PATENT DOCUMENTS

| | | |
|---|---|---|
| KR | 10-1452578 B1 | 10/2014 |
| KR | 10-2016-0079546 A | 7/2016 |
| KR | 10-2017-0070826 A | 6/2017 |
| KR | 10-2017-0083960 A | 7/2017 |

\* cited by examiner

ORGANIC ELECTROLUMINESCENCE DEVICE AND POLYCYCLIC COMPOUND FOR ORGANIC ELECTROLUMINESCENCE DEVICE

CROSS-REFERENCE TO RELATED APPLICATION

This application claims priority to and the benefit of Korean Patent Application No. 10-2018-0155173, filed on Dec. 5, 2018, the entire content of which is hereby incorporated by reference.

BACKGROUND

One or more aspects of example embodiments of the present disclosure are related to a polycyclic compound used as a luminescent material, and an organic electroluminescence device including the same.

Organic electroluminescence displays are being actively developed as image displays. An organic electroluminescence display differs from a liquid crystal display in that it is a self-luminescent display, in which holes and electrons injected from a first electrode and a second electrode, respectively, are recombined in an emission layer so that light is emitted from an organic luminescent material in the emission layer.

In application of an organic electroluminescence device to a display, decreased driving voltage, increased emission efficiency, and extended lifetimes for the organic electroluminescence device are desired, and development of materials that may reliably enable such features are desired.

For example, materials capable of phosphorescence emission using triplet state energy or delayed fluorescence emission using triplet-triplet annihilation (TTA) (in which singlet excitons are generated by the collision of triplet excitons) are being developed for a high efficiency organic electroluminescence device. In addition, thermally activated delayed fluorescence (TADF) materials using delayed fluorescence phenomenon are being developed.

SUMMARY

One or more aspects of embodiments of the present disclosure are directed toward an organic electroluminescence device with improved emission efficiency and device life.

One or more aspects of embodiments of the present disclosure are directed toward a polycyclic compound which may improve the emission efficiency and life of an organic electroluminescence device.

One or more example embodiments of the present disclosure provide a polycyclic compound represented by Formula 1:

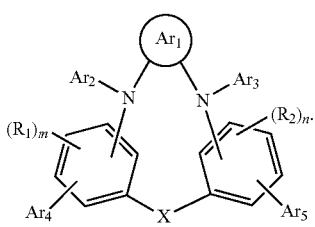

Formula 1

In Formula 1, X may be S, O, C(=O), $NR_a$, or $BR_b$; and $R_1$, $R_2$, $R_a$, and $R_b$ may each independently be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 5 to 30 carbon atoms for forming a ring. In some embodiments, two or more of $R_1$, $R_2$, $R_a$, and $R_b$ may form a ring by combining adjacent groups with each other. m and n may each independently be an integer of 0 to 3; $Ar_1$ to $Ar_3$ may each independently be a hydrocarbon ring having 5 to 60 carbon atoms for forming a ring or a heterocycle having 5 to 60 carbon atoms for forming a ring, in which no nitrogen atom is included in the ring; and $Ar_4$ and $Ar_5$ may each independently be represented by Formula 2:

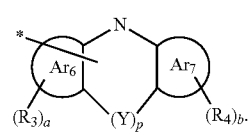

Formula 2

In Formula 2, p may be 0 or 1, and when p is 1, Y may be a direct linkage or $CR_cR_d$. $Ar_6$ and $Ar_7$ may each independently be a hydrocarbon ring having 5 to 60 carbon atoms for forming a ring or a heterocycle having 5 to 60 carbon atoms for forming a ring, in which no nitrogen atom is included in the ring. $R_3$, $R_4$, $R_c$, and $R_d$ may each independently be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 5 to 30 carbon atoms for forming a ring, and in some embodiments, two or more of $R_3$, $R_4$, $R_c$, and $R_d$ may form a ring when combined with adjacent groups; and a and b may each independently be an integer of 0 to 4.

In an embodiment, Formula 1 may be represented by Formula 1-1:

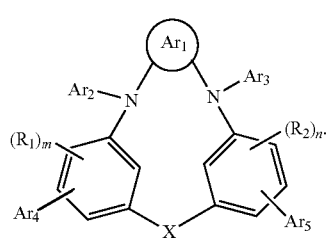

Formula 1-1

In Formula 1-1, X, $Ar_1$ to $Ar_5$, $R_1$, $R_2$, m, and n may each independently be the same as defined in connection with Formula 1.

In an embodiment, $Ar_1$ may each independently be a substituted or unsubstituted phenylene group.

In an embodiment, Formula 1 may be represented by Formula 1-2A or 1-2B:

Formula 1-2A

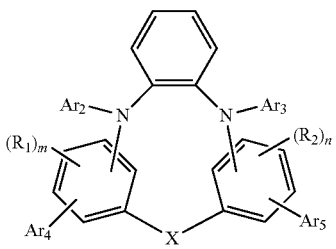

Formula 1-2B

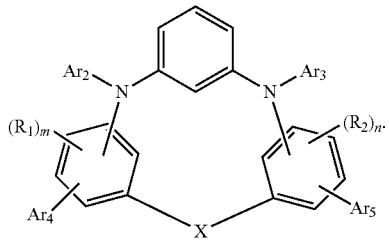

In Formulae 1-2A and 1-2B, X, $Ar_2$ to $Ar_5$, $R_1$, $R_2$, m, and n may each independently be the same as defined in connection with Formula 1.

In an embodiment, Formula 1 may be represented by Formula 1-3A or 1-3B:

Formula 1-3A

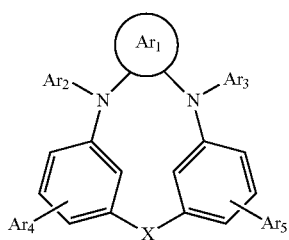

Formula 1-3B

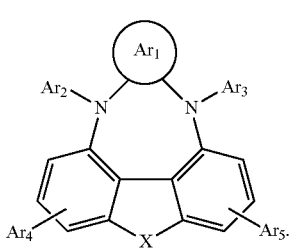

In Formulae 1-3A and 1-3B, X, and $Ar_1$ to $Ar_5$ may each independently be the same as defined in connection with Formula 1.

In an embodiment, Formula 2 may be represented by Formula 2-1 or 2-2:

Formula 2-1

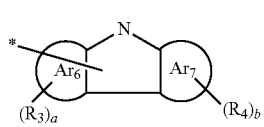

Formula 2-2

In Formulae 2-1 and 2-2, $Ar_6$, $Ar_7$, $R_3$, $R_4$, a, and b may each independently be the same as defined in connection with Formula 2.

In an embodiment, $Ar_2$ and $Ar_3$ may each independently be a substituted or unsubstituted phenyl group.

In an embodiment, $Ar_4$ and $Ar_5$ may be the same as each other.

In an embodiment, the polycyclic compound represented by Formula 1 may be a thermally activated delayed fluorescence material.

In an embodiment of the present disclosure, an organic electroluminescence device includes a first electrode; a hole transport region on the first electrode; an emission layer on the hole transport region, the emission layer including the polycyclic compound represented by Formula 1; an electron transport region on the emission layer; and a second electrode on the electron transport region. The first electrode and the second electrode each independently include at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, or an oxide thereof.

In an embodiment, the emission layer may be to emit delayed fluorescence.

In an embodiment, the emission layer may be a delayed fluorescence emission layer including a host and a dopant, and the dopant may include the polycyclic compound represented by Formula 1.

In an embodiment, the emission layer may be to emit blue light.

In an embodiment, the emission layer may be provided by an inkjet process.

BRIEF DESCRIPTION OF THE FIGURES

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
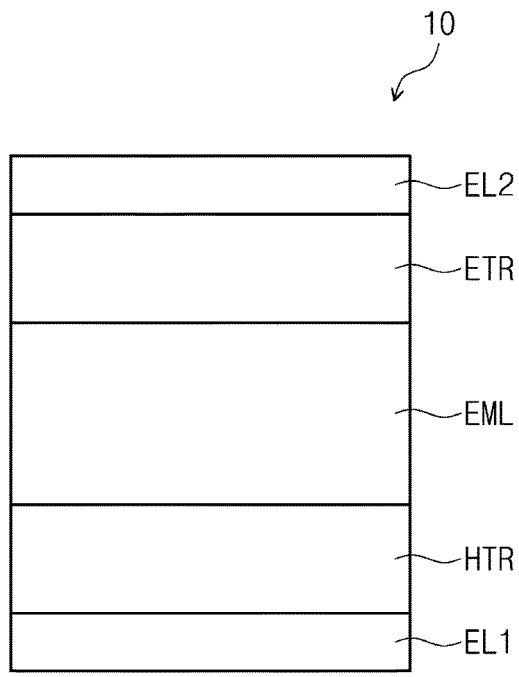
FIG. 1 is a schematic cross-sectional view of an organic electroluminescence device according to an embodiment of the present disclosure.

The present disclosure may have various modifications and may be embodied in different forms, and example embodiments will be explained in detail with reference to the accompanying drawings. However, the present disclosure should not be construed as being limited to the embodiments set forth herein. Rather, it should be understood that the scope of the present disclosure includes all modifications, equivalents, and alternatives within the spirit and scope of the present disclosure as hereinafter claimed.

In the present disclosure, it will be understood that when an element (or region, layer, part, etc.) is referred to as being "on", "connected to" or "coupled to" another element, it can be directly on/connected/coupled to the other element or intervening elements may be present. In contrast, when an element is referred to as being "directly on/connected/coupled" to another element, no intervening elements are present.

Like reference numerals refer to like elements for explaining each drawing, and duplicative descriptions thereof may not be provided. In the drawings, the thickness, the ratio and the dimension of each element may be exaggerated for effective description of the technical contents.

As used herein, the term "and/or" includes any and all combinations of one or more of the associated listed items. Expressions such as "at least one of", "one of", "selected from", "at least one selected from", and "one selected from", when preceding a list of elements, modify the entire list of elements and do not modify the individual elements of the list. Further, the use of "may" when describing embodiments of the present disclosure refers to "one or more embodiments of the present disclosure."

It will be understood that although the terms "first", "second", etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

Spatially relative terms, such as "beneath", "below", "above", "upper" and the like, are used herein to describe one element or feature's relationship to another element(s) or feature(s) as illustrated in the figures. It will be understood that the spatially relative terms are a relative concept to describe based on the orientation depicted in the figures.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be understood that the terms "include", "comprise", or "have," when used in this specification, specify the presence of stated features, numerals, steps, operations, elements, parts, or a combination thereof, but do not preclude the presence or addition of one or more other features, numerals, steps, operations, elements, parts, or a combination thereof.

Hereinafter, an organic electroluminescence device according to an embodiment of the present disclosure and a polycyclic compound according to an embodiment of the present disclosure to be included therein will be explained by referring to the accompanying drawings.

Figure 2:
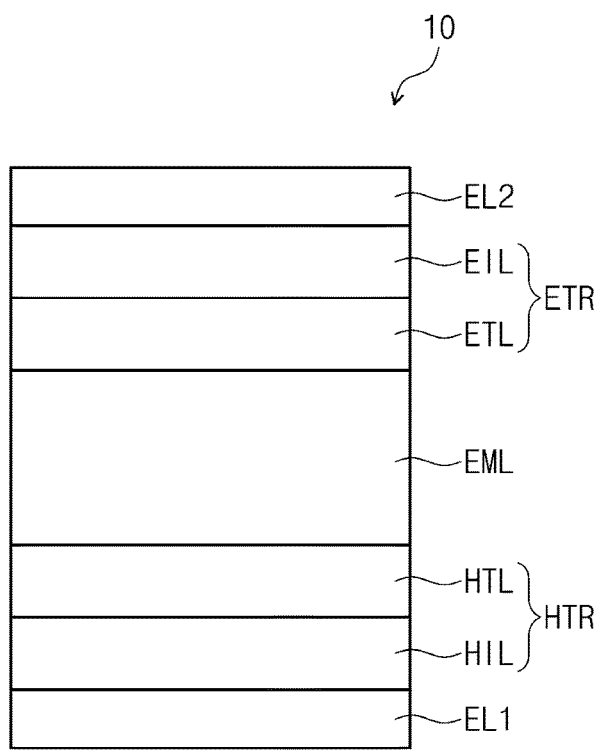
FIG. 2 is a schematic cross-sectional view of an organic electroluminescence device according to an embodiment of the present disclosure.
Figure 3:
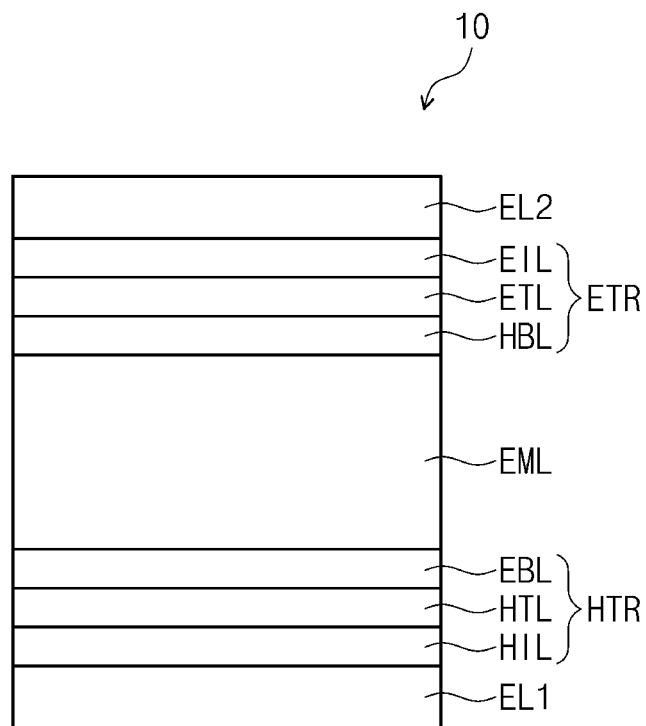
FIG. 3 is a schematic cross-sectional view of an organic electroluminescence device according to an embodiment of the present disclosure.

Each of FIGS. 1 to 3 is a schematic cross-sectional view illustrating an organic electroluminescence device according to an embodiment of the present disclosure. Referring to FIGS. 1 to 3, in the organic electroluminescence device 10 according to an embodiment of the present disclosure, the first electrode EL1 and the second electrode EL2 are oppositely positioned, and a plurality of organic layers are between the first electrode EL1 and the second electrode EL2. The plurality of organic layers may include a hole transport region HTR, an emission layer EML, and an electron transport region ETR. For example, the organic electroluminescence device 10 according to an embodiment of the present disclosure may include a first electrode EL1, a hole transport region HTR, an emission layer EML, an electron transport region ETR, and a second electrode EL2, laminated in that stated order. At least one of the plurality of organic layers may be formed by an inkjet process. For example, the organic layers of a hole transport region HTR, an emission layer EML, and an electron transport region ETR, etc. may be formed by an inkjet process. In some embodiments, the emission layer EML may be provided by an inkjet process.

The organic electroluminescence device 10 according to an embodiment of the present disclosure may include a polycyclic compound according to an embodiment of the present disclosure in the emission layer EML between the first electrode EL1 and the second electrode EL2. However, embodiments of the present disclosure are not limited thereto. The organic electroluminescence device 10 may further include the polycyclic compound according to an embodiment of the present disclosure in at least one of the plurality of organic layers between the first electrode EL1 and the second electrode EL2, in addition to the emission layer EML. For example, the organic electroluminescence device 10 according to an embodiment of the present disclosure may include the polycyclic compound in the emission layer EML as a luminescent material, and in some embodiments, may further include the polycyclic compound in at least one of the organic layers included in the hole transport region HTR and the electron transport region ETR.

Compared with FIG. 1, FIG. 2 shows a schematic cross-sectional view illustrating an organic electroluminescence device 10 according to an embodiment of the present disclosure, in which the hole transport region HTR includes a hole injection layer HIL and a hole transport layer HTL, and the electron transport region ETR includes an electron injection layer EIL and an electron transport layer ETL. Compared with FIG. 1, FIG. 3 shows a schematic cross-sectional view illustrating an organic electroluminescence device 10 according to an embodiment of the present disclosure, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL.

The first electrode EL1 has conductivity (e.g., may be conductive). The first electrode EL1 may be formed of a metal alloy and/or a conductive compound. The first electrode EL1 may be an anode. The first electrode EL1 may also (e.g., simultaneously) be a pixel electrode. The first electrode EL1 may be a transmissive electrode, a transflective (semi-transmissive) electrode, or a reflective electrode. When the first electrode EL1 is a transmissive electrode, the first electrode EL1 may include or be formed of a transparent metal oxide (such as indium tin oxide (ITO), indium zinc oxide (IZO), zinc oxide (ZnO), and/or indium tin zinc oxide (ITZO)). When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), a compound thereof, or a mixture thereof (for example, a mixture of Ag and Mg). The first electrode EL1 may have a structure including a plurality of layers including a reflective layer or transflective layer formed using the above materials, and a transparent conductive layer formed using ITO, IZO, ZnO, or ITZO. For example, the first electrode EL1 may have a triple-layer structure of ITO/Ag/ITO. However, embodiments of the present disclosure are not limited thereto. The thickness of the first electrode EL1 may be about 1,000 Å to about 10,000 Å, for example, about 1,000 Å to about 3,000 Å.

The hole transport region HTR is on the first electrode EL1. The hole transport region HTR may include at least one selected from a hole injection layer HIL, a hole transport layer HTL, a hole buffer layer, and an electron blocking layer EBL. The thickness of the hole transport region HTR may be, for example, about 50 Å to about 15,000 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure including one selected from a hole injection layer HIL and a hole transport layer HTL, or may have a single layer structure formed using a hole injection material and a hole transport material. In addition, the hole transport region HTR may have a single layer structure formed using a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, laminated in order from the first electrode EL1, without limitation.

The hole transport region HTR may be formed using any suitable method (such as a vacuum deposition method, a spin coating method, a cast method, a Langmuir-Blodgett (LB) method, an inkjet printing method, a laser printing method, and a laser induced thermal imaging (LITI) method).

The hole injection layer HIL may include, for example, a phthalocyanine compound (such as copper phthalocyanine); N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalen-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h] quinoxaline-2,3,6,7,10,11-hexacarbonitrile (HAT-CN), etc.

The hole transport layer HTL may further include one or more carbazole derivatives (such as N-phenyl carbazole and polyvinyl carbazole), fluorene-based derivatives, N,N'-bis(3-methylphenyl)-N,N'-diphenyl-[1,1-biphenyl]-4,4'-diamine (TPD), triphenylamine-based derivatives (such as 4,4',4''-tris(N-carbazolyl)triphenylamine (TCTA)), N,N'-di(naphthalen-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be about 50 Å to about 10,000 Å, for example, about 100 Å to about 5,000 Å. The thickness of the hole injection layer HIL may be, for example, about 30 Å to about 1,000 Å, and the thickness of the hole transport layer HTL may be about 10 Å to about 1,000 Å. For example, the thickness of the electron blocking layer EBL may be about 10 Å to about 1,000 Å. When the thicknesses of the hole transport region HTR, the hole injection layer HIL, the hole transport layer HTL and the electron blocking layer EBL satisfy the above-described ranges, satisfactory hole transport properties may be obtained without a substantial increase in driving voltage.

The hole transport region HTR may further include a charge generating material in addition to the above-described materials to improve conductivity. The charge generating material may be dispersed in the hole transport region HTR uniformly or non-uniformly. The charge generating material may be, for example, a p-dopant. The p-dopant may be a quinone derivative, metal oxide, or cyano group-containing compound, without limitation. Non-limiting examples of the p-dopant may include quinone derivatives (such as tetracyanoquinodimethane (TCNQ) and 2,3,5,6-tetrafluoro-7,7,8,8-tetracyanoquinodimethane (F4-TCNQ)), and metal oxides (such as tungsten oxide and molybdenum oxide).

As described above, the hole transport region HTR may further include at least one selected from a hole buffer layer and an electron blocking layer EBL in addition to the hole injection layer HIL and the hole transport layer HTL. The hole buffer layer may compensate for an optical resonance distance according to the wavelength of light emitted from the emission layer EML (e.g., be used to adjust the optical resonance distance to match the wavelength of light emitted from the emission layer) to thereby increase light emission efficiency. Materials included in the hole transport region HTR may be used in the hole buffer layer. The electron blocking layer EBL may prevent or reduce electron injection from the electron transport region ETR into the hole transport region HTR.

The emission layer EML is on the hole transport region HTR. The thickness of the emission layer EML may be, for example, about 100 Å to about 1,000 Å, or about 100 Å to about 300 Å. The emission layer EML may have a single layer formed using a single material, a single layer formed using a plurality of different materials, or a multilayer structure having a plurality of layers formed using a plurality of different materials.

In the organic electroluminescence device 10 according to an embodiment of the present disclosure, the emission layer EML may include a polycyclic compound according to an embodiment of the present disclosure.

The polycyclic compound according to an embodiment of the present disclosure may include a plurality of electron donors and an electron acceptor between the electron donors. The electron acceptor may connect (e.g., link) the electron donors with each other. The electron acceptor may combine (e.g., be combined) with the plurality of electron donors. For example, the polycyclic compound according to an embodiment of the present disclosure may include two electron donors and one electron acceptor.

In the polycyclic compound according to an embodiment of the present disclosure, the electron acceptor may have a fixed conformation by an arylamino moiety. For example, the electron acceptor may combine with the arylamino moieties to form a condensed ring. In the polycyclic compound of an embodiment, the electron acceptor may combine with the arylamino moieties to form a condensed ring, and therefore, the polycyclic compound may have a planar conformation. Accordingly, in case the polycyclic compound of an embodiment is used as a luminescent material, half-width of emitted light may be reduced.

In the polycyclic compound according to an embodiment of the present disclosure, the electron donor (e.g., at least one of the plurality of electron donors) may be a substituted or unsubstituted carbazole group or a substituted or unsubstituted diarylamino group. Furthermore, in the polycyclic compound, the electron acceptor may include a sulfur atom (S), an oxygen atom (O), C(=O), $NR_a$, or $BR_b$, etc. $R_a$ and $R_b$ may each be the same as described in connection with Formula 1 below.

In the present disclosure, the term "substituted or unsubstituted" indicates that the following group or moiety may be unsubstituted, or alternatively, substituted with at least one substituent selected from the group consisting of a deuterium atom, a halogen atom, a cyano group, a nitro group, an amino group, a silyl group, an oxy-containing group, a thio-containing group (e.g., a thiol group, thioalkyl group, etc.), a sulfinyl group, a sulfonyl group, a carbonyl group, a boron-containing group (e.g., a boryl group, a boronic acid group, a boronic ester group, etc.), a phosphine oxide group, a phosphine sulfide group, an alkyl group, an alkenyl group, an alkoxy group, a hydrocarbon ring, an aryl group, and a heterocyclic group (heterocycle). In addition, each of the substituents illustrated above may be further substituted or unsubstituted. For example, a biphenyl group may be interpreted as a unitary aryl group, or as a phenyl group substituted with a phenyl group.

In the present disclosure, the term "forming a ring by combining adjacent groups with each other" refers to forming a substituted or unsubstituted hydrocarbon ring or a substituted or unsubstituted heterocycle by combining (e.g., linking) groups with each other. The hydrocarbon ring includes an aliphatic hydrocarbon ring and an aromatic hydrocarbon ring. The heterocycle includes an aliphatic heterocycle and an aromatic heterocycle. The ring formed by combining adjacent groups may be a monocycle or a polycycle. In addition, the ring formed by combining adjacent groups may be connected with another ring to form a spiro structure.

In the present disclosure, the term "an adjacent group" refers to a substituent on an atom that is directly connected to the base atom of the present substituent, another substituent on the same base atom of the present substituent, and/or a substituent stereoscopically positioned (e.g., in three-dimensional space) near or within bonding distance of the present substituent. For example, two methyl groups in 1,2-dimethylbenzene may be interpreted as "adjacent groups", and two ethyl groups in 1,1-diethylcyclopentane may also be interpreted as "adjacent groups".

Non-limiting examples of a halogen atom include a fluorine atom, a chlorine atom, a bromine atom, and an iodine atom.

In the present disclosure, the alkyl group may have a linear, branched or cyclic form. The carbon number of the alkyl group may be 1 to 50, 1 to 30, 1 to 20, 1 to 10, or 1 to 6. Non-limiting examples of the alkyl group include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc.

In the present disclosure, the hydrocarbon ring may be an aliphatic hydrocarbon ring or an aromatic hydrocarbon ring. The heterocycle may be an aliphatic heterocycle or an aromatic heterocycle. Each hydrocarbon ring and heterocycle may independently be a monocycle or a polycycle.

In the present disclosure, the hydrocarbon ring may be any functional group or substituent derived from an aliphatic hydrocarbon ring, or any functional group or substituent derived from an aromatic hydrocarbon ring. The carbon number of the hydrocarbon ring for forming a ring may be 5 to 60.

In the present disclosure, the heterocycle may be any functional group or substituent derived from a heterocycle including at least one heteroatom for forming a ring. The carbon number of the heterocycle for forming a ring may be 5 to 60.

In the present disclosure, the aryl group may be any functional group or substituent derived from an aromatic hydrocarbon ring. The aryl group may be monocyclic aryl or polycyclic aryl. The carbon number of the aryl group for forming a ring may be 6 to 30, 6 to 20, or 6 to 15. Non-limiting examples of the aryl group include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc.

In the present disclosure, the fluorenyl group may be substituted, and two substituents (e.g., at the 9-H position) may be combined with each other to form a spiro structure. Non-limiting examples of the substituted fluorenyl group include the following groups:

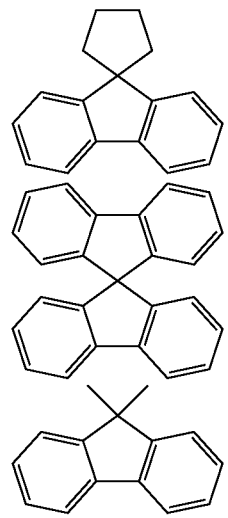

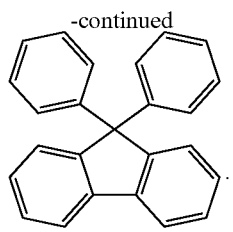

In the present disclosure, the heteroaryl group may be a heteroaryl including at least one of B, O, N, P, Si, or S as a heteroatom. When the heteroaryl group includes two or more heteroatoms, these heteroatoms may be the same or different from each other. The heteroaryl group may be monocyclic heterocycle or polycyclic heterocycle. The carbon number of the heteroaryl group for forming a ring may be 2 to 30, 2 to 20, or 2 to 10. Non-limiting examples of the heteroaryl group include thiophene, furan, pyrrole, imidazole, thiazole, oxazole, oxadiazole, triazole, pyridine, bipyridine, pyrimidine, triazine, acridine, pyridazine, pyrazine, quinoline, quinazoline, quinoxaline, phenoxazine, phthalazine, pyrido pyrimidine, pyrido pyrazine, pyrazino pyrazine, isoquinoline, indole, carbazole, N-aryl carbazole, N-heteroaryl carbazole, N-alkyl carbazole, benzoxazole, benzimidazole, benzothiazole, benzocarbazole, benzothiophene, dibenzothiophene, thienothiophene, benzofuran, phenanthroline, thiazole, isoxazole, thiadiazole, phenothiazine, dibenzosilole, dibenzofuran, etc.

In the present disclosure, the above explanation on the aryl group may be applied to the arylene group, except that the arylene group is divalent. The above explanation on the heteroaryl group may be applied to the heteroarylene group, except that the heteroarylene group is divalent.

In the present disclosure, the silyl group includes alkyl silyl and aryl silyl. Non-limiting examples of the silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc.

In the present disclosure, the carbon number of the amino group is not specifically limited, and may be 1 to 30. The amino group may include alkyl amino and aryl amino. Non-limiting examples of the amino group include methylamino, dimethylamino, phenylamino, diphenylamino, naphthylamino, 9-methyl-anthracenylamino, triphenylamino, etc.

In the present disclosure, —* indicates a position of connection to another formula, moiety, or group.

In the organic electroluminescence device 10 according to an embodiment of the present disclosure, the emission layer EML may include a polycyclic compound represented by Formula 1:

Formula 1

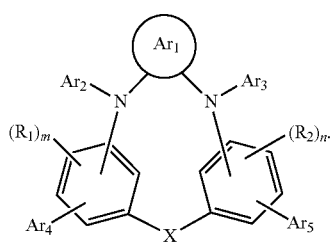

In Formula 1, X may be S, O, C(=O), NR$_a$, or BR$_b$. In Formula 1, R$_1$, R$_2$, R$_a$, and R$_b$ may each independently be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 5 to 30 carbon atoms for forming a ring, and in some embodiments, adjacent groups may combine with each other to form a ring. m and n may each independently be an integer of 0 to 3. When m and n are each an integer of 2 or more, a plurality of R$_1$ and/or a plurality of R$_2$ may be the same or different from each other.

In Formula 1, Ar$_1$ to Ar$_3$ may be each independently a hydrocarbon ring having 5 to 60 carbon atoms for forming a ring, or a heterocycle having 5 to 60 carbon atoms for forming a ring, in which no nitrogen atom is included in the ring, and Ar$_4$ and Ar$_5$ may each independently be represented by Formula 2:

Formula 2

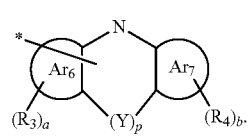

In Formula 2, p may be 0 or 1, and when p is 1, Y may be a direct linkage or CR$_c$R$_d$. In Formula 2, Ar$_6$ and Ar$_7$ may each independently be a hydrocarbon ring having 5 to 60 carbon atoms for forming a ring, or a heterocycle having 5 to 60 carbon atoms for forming a ring, in which no nitrogen atom is included in the ring.

In Formula 2, R$_3$, R$_4$, R$_c$, and R$_d$ may each independently be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 5 to 30 carbon atoms for forming a ring, and in some embodiments, adjacent groups may combine with each other to form a ring. In addition, a and b may each independently be an integer of 0 to 4. When a and b are each an integer of 2 or more, a plurality of R$_3$ or a plurality of R$_4$ may be the same or different from each other.

In the polycyclic compound represented by Formula 1 according to an embodiment of the present disclosure, Ar$_4$ and Ar$_5$ may each independently be an electron donor and the core moiety including X may be an electron acceptor. For example, the polycyclic compound represented by Formula 1 according to an embodiment of the present disclosure may have a structure of electron donor-electron acceptor-electron donor.

In the polycyclic compound according to an embodiment of the present disclosure, the electron acceptor including X may have a fixed ring structure combined with an arylamine moiety, for example, according to the following:

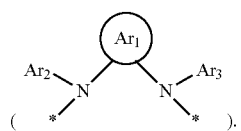

In Formula 1, Ar$_1$ may be a substituted or unsubstituted hydrocarbon ring having 5 to 60 carbon atoms for forming a ring. For example, Ar$_1$ may be a substituted or unsubstituted aromatic hydrocarbon ring having 5 to 60 carbon atoms for forming a ring. For example, in the polycyclic compound according to an embodiment of the present disclosure, $Ar_1$ may be a substituted or unsubstituted phenylene group.

In the polycyclic compound represented by Formula 1, $Ar_2$ and $Ar_3$ may each independently be a hydrocarbon ring having 5 to 60 carbon atoms for forming a ring, or a heterocycle having 5 to 60 carbon atoms for forming a ring, in which no nitrogen atom is included in the ring. For example, $Ar_2$ and $Ar_3$ may each independently be a substituted or unsubstituted aromatic hydrocarbon ring having 5 to 60 carbon atoms for forming a ring. For example, in the polycyclic compound, $Ar_2$ and $Ar_3$ may each independently be a substituted or unsubstituted phenyl group.

In an embodiment, $Ar_2$ and $Ar_3$ may be the same as each other. For example, $Ar_2$ and $Ar_3$ may each be an unsubstituted phenyl group.

In the polycyclic compound represented by Formula 1 according to an embodiment of the present disclosure, the arylamine moiety may combine with the electron acceptor to fix the electron acceptor on a planar conformation (e.g., so that the electron acceptor assumes a substantially fixed, substantially planar conformation). In the polycyclic compound according to an embodiment of the present disclosure, the arylamine moiety may be represented by Formula A:

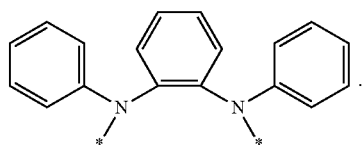

Formula A

In Formula A, "———*" may refer to a point of connection with a phenylene linker in the core moiety of Formula 1.

In the polycyclic compound represented by Formula 1 according to an embodiment of the present disclosure, $R_1$ and $R_2$ may each independently be a hydrogen atom, a deuterium atom, a halogen atom, an alkyl group having 1 to 10 carbon atoms, a substituted or unsubstituted aryl group having 6 to 30 carbon atoms for forming a ring, or a substituted or unsubstituted heteroaryl group having 5 to 30 carbon atoms for forming a ring. Alternatively, adjacent $R_1$ and $R_2$ groups may form a ring by being combined with each other.

For example, $R_1$ and $R_2$ may each independently be a hydrogen atom or an alkyl group having 1 to 10 carbon atoms. In some embodiments, adjacent $R_1$ and $R_2$ may combine with each other to form a hydrocarbon ring or a heterocycle including X for forming a ring. For example, in the polycyclic compound represented by Formula 1, the phenylene ring substituted with $R_1$ may combine with the phenylene ring substituted with $R_2$ to form a fluorenone moiety, a dibenzothiophene moiety, or a dibenzofuran moiety, etc.

In Formula 1, $Ar_4$ and $Ar_5$ may each independently be represented by Formula 2, and Formula 2 may be further represented by Formula 2-1 or 2-2. Formula 2-1 is an embodiment of Formula 2 in which p is 1 and Y is a direct linkage, and Formula 2-2 is an embodiment of Formula 2 in which p is 0.

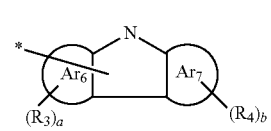

Formula 2-1

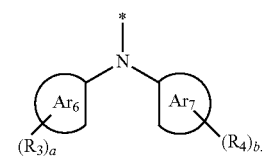

Formula 2-2

In Formulae 2, 2-1 and 2-2, $Ar_6$ and $Ar_7$ may each independently be a hydrocarbon ring having 5 to 60 carbon atoms for forming a ring, or a heterocycle having 5 to 60 carbon atoms for forming a ring, in which no nitrogen atom is included in the ring.

In an embodiment, $Ar_6$ and $Ar_7$ may be the same as each other. In an embodiment, $Ar_6$ and $Ar_7$ may each independently be a hydrocarbon ring having 5 to 60 carbon atoms for forming a ring. For example, $Ar_6$ and $Ar_7$ may each independently be an aromatic hydrocarbon ring having 5 to 60 carbon atoms for forming a ring. For example, $Ar_6$ and $Ar_7$ may each be a benzene ring.

For example, $Ar_6$ and $Ar_7$ may each independently be represented by D1 or D2:

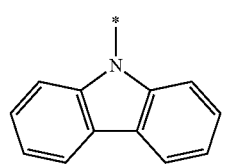

D1

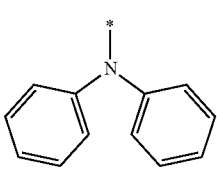

D2

For example, Formula 2-1 may be a substituted or unsubstituted carbazole group, and Formula 2-2 may be a substituted or unsubstituted diphenylamine group.

In some embodiments, in the polycyclic compound represented by Formula 1, $Ar_4$ and $Ar_5$ may be the same as each other.

In some embodiments, the polycyclic compound represented by Formula 1 may be further represented by Formula 1-1:

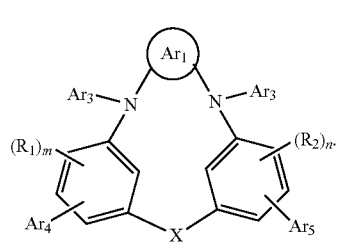

Formula 1-1

Formula 1-1 is an embodiment of Formula 1 in which the binding position of the arylamine moiety is specified. For example, in the polycyclic compound represented by Formula 1-1, the arylamine moiety and X may be connected to the phenylene linker at a meta position.

In Formula 1-1, X, $Ar_1$ to $Ar_5$, $R_1$, $R_2$, m, and n may each independently be the same as described in connection with Formula 1.

In some embodiments, Formula 1 may be represented by Formula 1-2A or 1-2B:

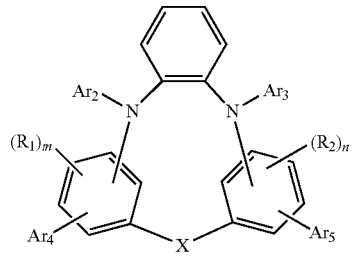

Formula 1-2A

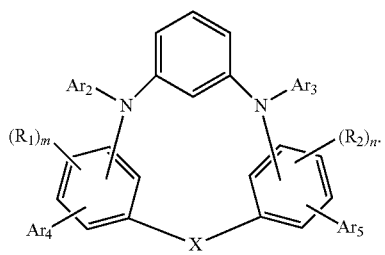

Formula 1-2B

In Formulae 1-2A and 1-2B, X, $Ar_2$ to $Ar_5$, $R_1$, $R_2$, m, and n may each independently be the same as described in connection with Formula 1.

Each of Formulae 1-2A and 1-2B is an embodiment of Formula 1 in which $Ar_1$ is a phenylene group. Formula 1-2A is different from Formula 1-2B in the relative positions of the arylamine groups connected to the $Ar_1$ phenylene. In Formula 1-2A, the arylamine groups (*—$NAr_2$ and *—$NAr_3$) are connected to phenylene in ortho positions. In Formula 1-2B, the arylamine groups (*—$NAr_2$ and *—$NAr_3$) are connected to phenylene in meta positions.

The polycyclic compound represented by Formula 1 according to an embodiment of the present disclosure may be further represented by Formula 1-3A or 1-3B. Formula 1-3A is an embodiment of Formula 1 in which both m and n are 0, or both $R_1$ and $R_2$ are a hydrogen atom. Formula 1-3B is an embodiment of Formula 1 in which adjacent $R_1$ and $R_2$ groups combine with each other to form a ring. For example, Formula 1-3B is an embodiment of Formula 1 in which adjacent $R_1$ and $R_2$ combine with each other to form a ring including X.

Formula 1-3A

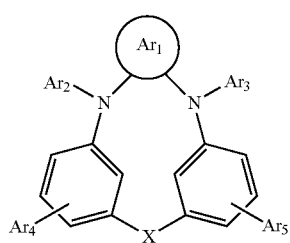

Formula 1-3B

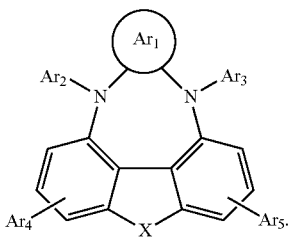

In Formulae 1-3A and 1-3B X and $Ar_1$ to $Ar_5$ may each independently be the same as described in connection with Formula 1.

In some embodiments, for example, Formula 1-3B may be represented by any one of Formulae 3-a to 3-e. In Formulae 3-a to 3-e, $Ar_1$ to $Ar_5$ may be the same as described in connection with Formula 1:

3-a

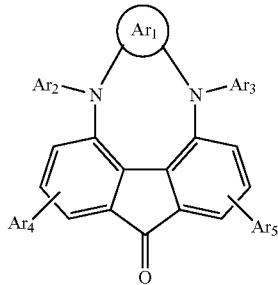

3-b

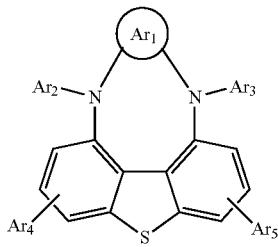

3-c

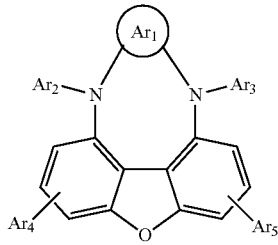

3-d

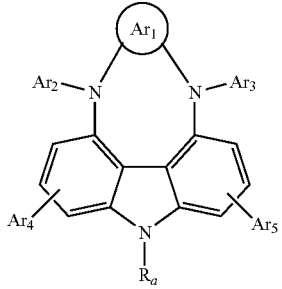

3-e
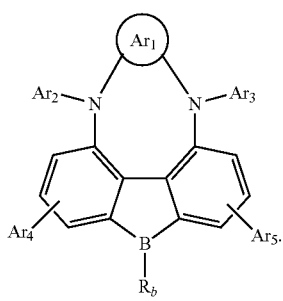
The polycyclic compound according to an embodiment of the present disclosure may be any one of the compounds represented in Compound Group 1:
Compound Group 1
A-1
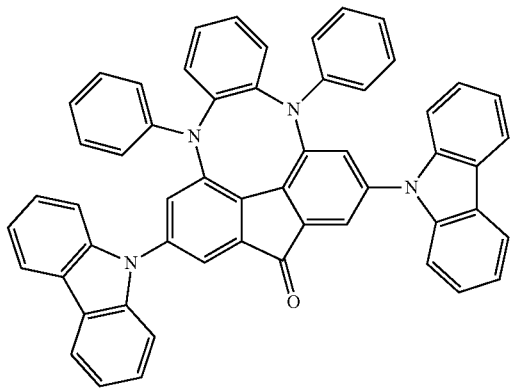
A-2
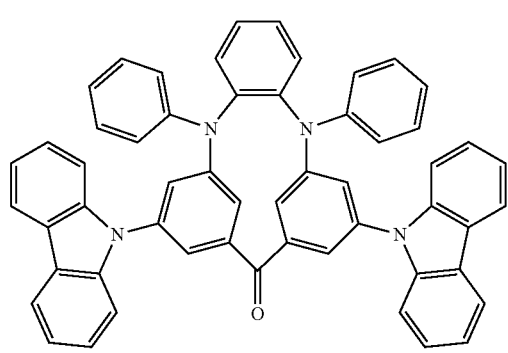
A-3
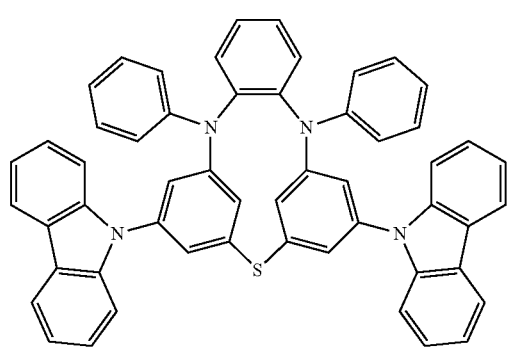
A-4
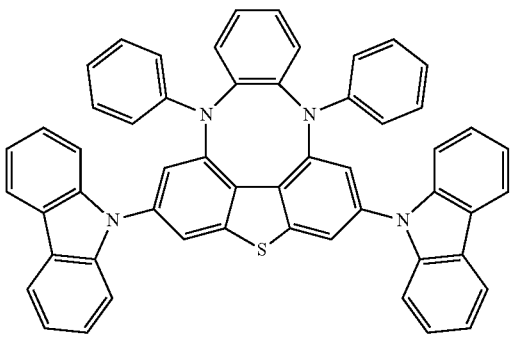
A-5
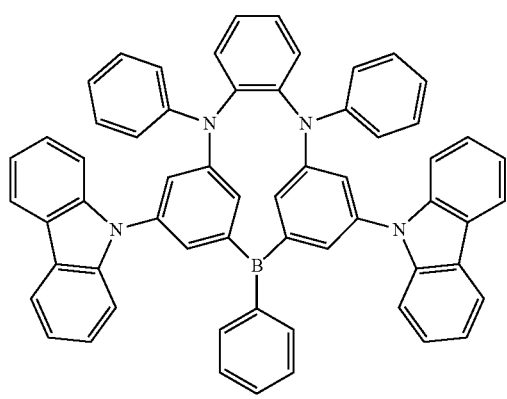
A-6
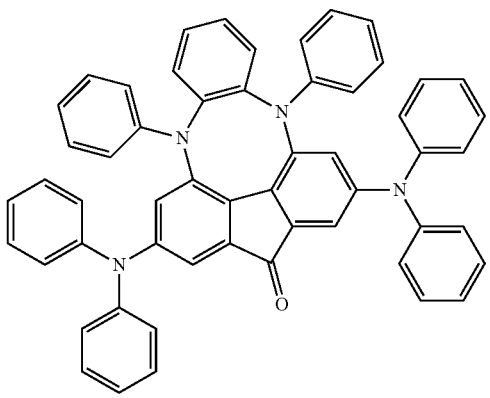
A-7
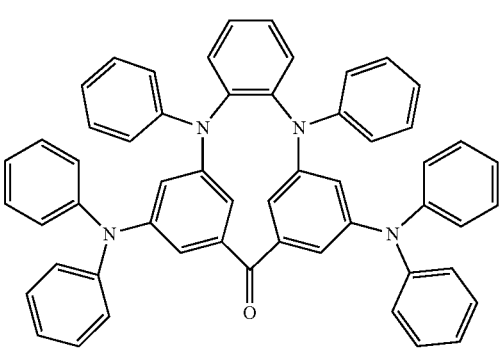

-continued
A-8
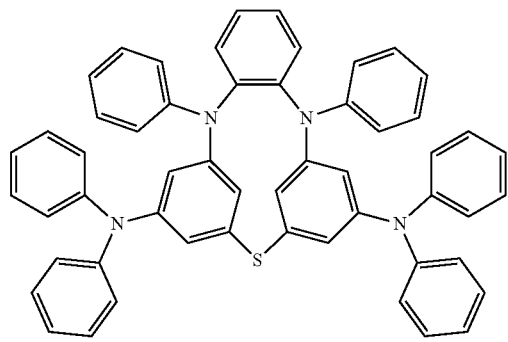
A-9
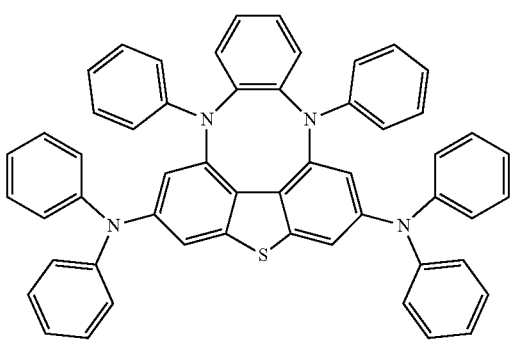
A-10
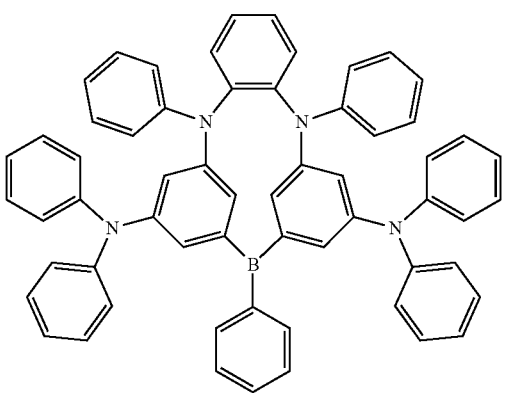
A-11
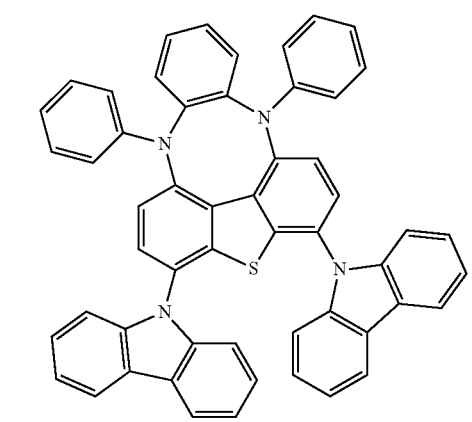
A-12
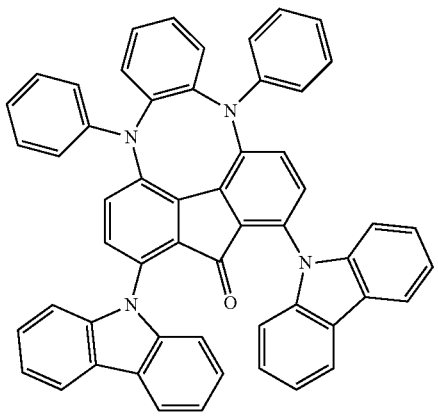
A-13
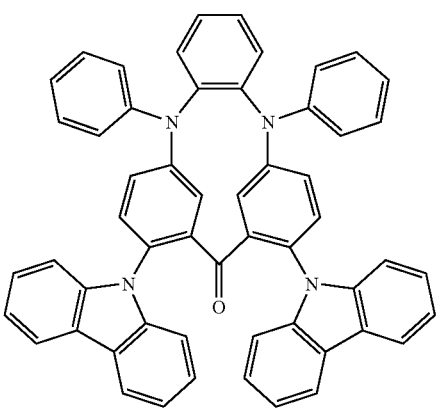
A-14
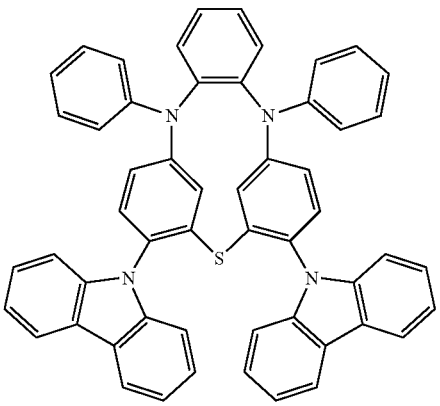
A-15
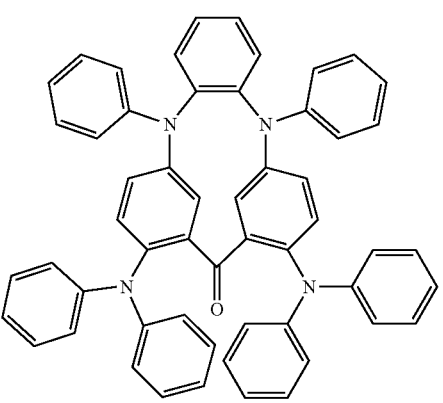

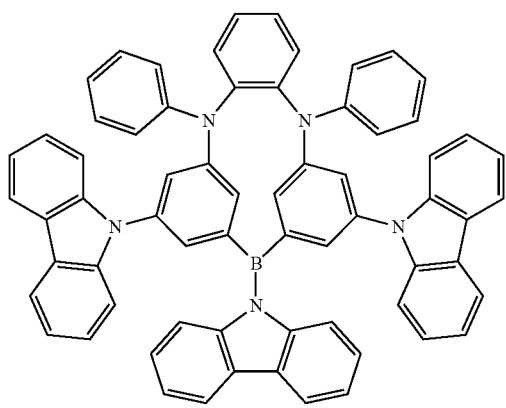
A-16
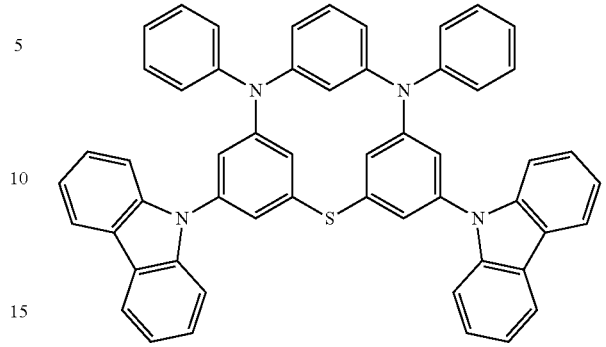
A-20
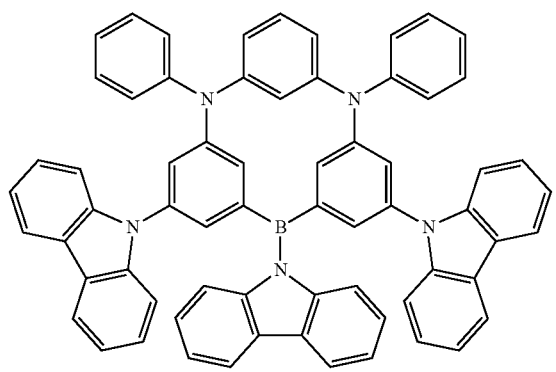
A-17
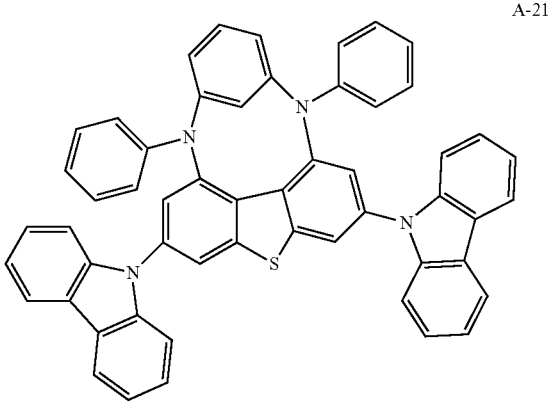
A-21
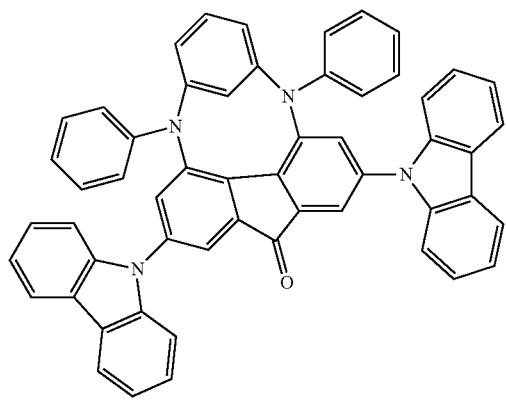
A-18
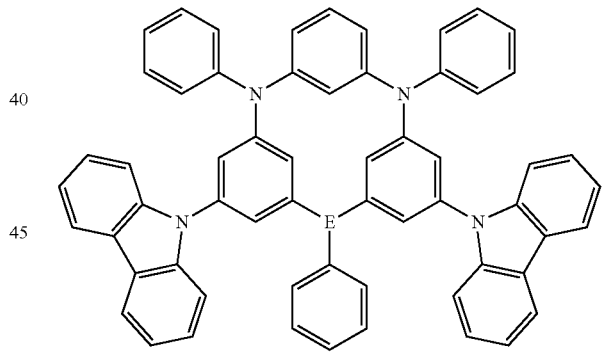
A-22
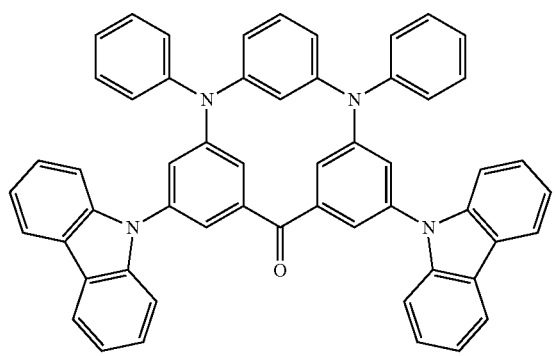
A-19
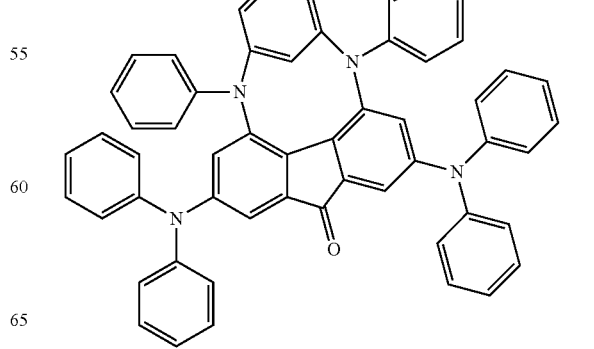
A-23

A-24
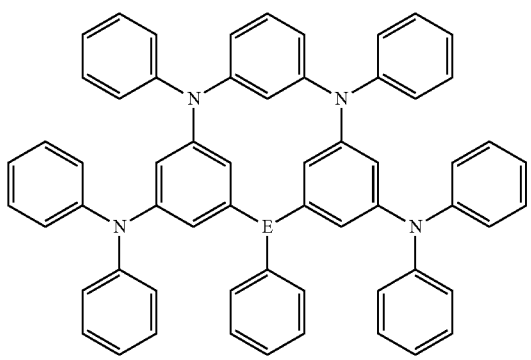

A-25
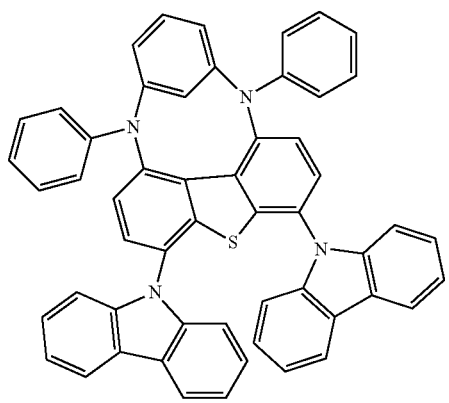

A-26
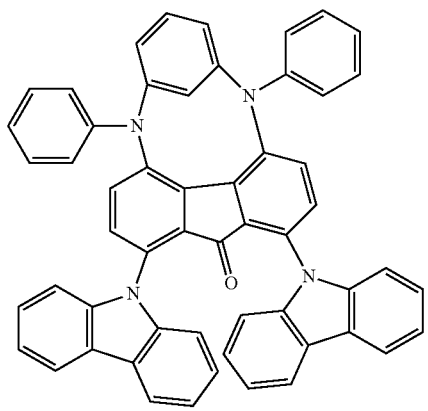

The organic electroluminescence device 10 according to an embodiment of the present disclosure may include at least one polycyclic compound represented in Compound Group 1 in the emission layer EML.

The polycyclic compound represented by Formula 1 may be a thermally activated delayed fluorescence material. In the organic electroluminescence device 10 according to an embodiment of the present disclosure, the emission layer EML may be to emit delayed fluorescence. For example, the emission layer EML may be to emit a thermally activated delayed fluorescence (TADF).

In the organic electroluminescence device 10, the emission layer EML may be to emit blue light. For example, in the organic electroluminescence device 10 according to an embodiment of the present disclosure, the emission layer EML may be to emit blue light with a wavelength range of about 480 nm or lower. However, embodiments of the present disclosure are not limited thereto, and the emission layer EML may be to emit red light and/or green light.

In some embodiments, the organic electroluminescence device 10 may include a plurality of emission layers. The plurality of emission layers may be provided as a stack of laminated layers, and the organic electroluminescence device 10 including the plurality of emission layers may be to emit white light, for example. In some embodiments, the organic electroluminescence device including the plurality of emission layers may be an organic electroluminescence device having a tandem structure. When the organic electroluminescence device 10 includes the plurality of emission layers, at least one emission layer EML may include at least one of the above-described polycyclic compounds according to an embodiment of the present disclosure.

In an embodiment, the emission layer EML may include a host and a dopant, and may include the above-described polycyclic compound as the dopant. For example, in the organic electroluminescence device 10, the emission layer EML may include a host for delayed fluorescence emission and a dopant for delayed fluorescence emission, and may include the above-described polycyclic compound as the dopant for delayed fluorescence emission. The emission layer EML may include at least one compound represented in Compound Group 1 as a thermally activated delayed fluorescence dopant.

In an embodiment, the emission layer EML may be a delayed fluorescence emission layer, and may include any suitable host material and the above-described polycyclic compound. For example, the polycyclic compound according to an embodiment of the present disclosure may be used as a TADF dopant.

In an embodiment, the emission layer EML may include any suitable host material. For example, the emission layer EML may include, as a host material, tris(8-hydroxyquinolino)aluminum (Alq3), 4,4'-bis(N-carbazolyl)-1,1'-biphenyl (CBP), poly(N-vinylcarbazole) (PVK), 9,10-di(naphthalene-2-yl)anthracene (ADN), 4,4',4"-tris(carbazol-9-yl)-triphenylamine (TCTA), 1,3,5-tris(1-phenyl-1H-benzo[d]imidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetrasiloxane (DPSiO$_4$), 2,8-bis(diphenylphosphoryl)dibenzofuran (PPF), 3,3'-bis(N-carbazolyl)-1,1'-biphenyl (mCBP), 1,3-bis(N-carbazolyl)benzene (mCP), etc. However, embodiments of the present disclosure are not limited thereto, and any suitable delayed fluorescence host material may be included in addition to the above host material.

In the organic electroluminescence device 10, the emission layer EML may further include any suitable dopant material. In an embodiment, the emission layer EML may include, as a dopant, styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi)), perylene and derivatives thereof (for example, 2,5,8,11-tetra-t-butylperylene (TBP)), pyrene and derivatives thereof (for example, 1,1-dipyrene, 1,4-dipyrenylbenzene and 1,4-bis(N,N-diphenylamino)pyrene), etc.

In the organic electroluminescence device 10 according to an embodiment of the present disclosure as shown in FIGS. 1 to 3, the electron transport region ETR is provided on the emission layer EML. The electron transport region ETR may include at least one selected from a hole blocking layer HBL, an electron transport layer ETL, and an electron injection layer EIL, without limitation.

The electron transport region ETR may have a single layer formed using a single material, a single layer formed using a plurality of different materials, or a multilayer structure having a plurality of layers formed using a plurality of different materials.

For example, the electron transport region ETR may have a single layer structure including an electron injection layer EIL or an electron transport layer ETL, or a single layer structure formed using an electron injection material and an electron transport material (e.g., in the same layer). In some embodiments, the electron transport region ETR may have a single layer structure having a plurality of different materials, or a laminated structure of electron transport layer ETL/electron injection layer EIL, or hole blocking layer HBL/electron transport layer ETL/electron injection layer EIL, laminated in each stated order from the emission layer EML, without limitation. The thickness of the electron transport region ETR may be, for example, about 1,000 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, and a laser induced thermal imaging (LITI) method).

When the electron transport region ETR includes the electron transport layer ETL, the electron transport region ETR may include an anthracene derivative. However, an embodiment of the present disclosure is not limited thereto. For example, the electron transport region may include tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-yl)phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-Biphenyl-4-olato)aluminum (BAIq), beryllium bis(benzoquinolin-10-olate) (Bebq$_2$), 9,10-di(naphthalen-2-yl)anthracene (ADN) and a mixture thereof. The thickness of the electron transport layer ETL may be about 100 Å to about 1,000 Å, for example, about 150 Å to about 500 Å. When the thickness of the electron transport layer ETL satisfies the above-described ranges, satisfactory electron transport properties may be obtained without a substantial increase in driving voltage.

When the electron transport region ETR includes the electron injection layer EIL, the electron transport region ETR may use LiF, lithium quinolate (LiQ), Li$_2$O, BaO, NaCl, CsF, a lanthanide metal (such as Yb), or a metal halide (such as RbCl and RbI). However, embodiments of the present disclosure are not limited thereto. In some embodiments, the electron injection layer EIL may be formed using a mixture of an electron transport material and an insulating organo metal salt. The organo metal salt may be a material having an energy band gap of about 4 eV or more. For example, the organo metal salt may include a metal acetate, a metal benzoate, a metal acetoacetate, a metal acetylacetonate, or a metal stearate. The thickness of the electron injection layer EIL may be about 1 Å to about 100 Å, for example, about 3 Å to about 90 Å. When the thickness of the electron injection layer EIL satisfies the above described ranges, satisfactory electron injection properties may be obtained without inducing a substantial increase in driving voltage.

The electron transport region ETR may include a hole blocking layer HBL, as described above. The hole blocking layer HBL may include, for example, at least one selected from 2,9-dimethyl-4,7-diphenyl-1,10-phenanthroline (BCP) and 4,7-diphenyl-1,10-phenanthroline (Bphen), without limitation.

The second electrode EL2 is on the electron transport region ETR. The second electrode EL2 may be a common electrode or a cathode. The second electrode EL2 may be a transmissive electrode, a transflective (semi-transmissive) electrode, or a reflective electrode. When the second electrode EL2 is a transmissive electrode, the second electrode EL2 may be formed using a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayer structure including a reflective layer or a transflective layer formed using the above-described materials and a transparent conductive layer formed using ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

In some embodiments, the organic electroluminescence device 10 according to an embodiment of the present disclosure may include a capping layer on the second electrode EL2. The capping layer may include, for example, α-NPD, NPB, TPD, m-MTDATA, Alq3, CuPc, N4,N4,N4', N4'-tetra(biphenyl-4-yl)biphenyl-4,4'-diamine (TPD15), 4,4',4''-tris(carbazol-9-yl)-triphenylamine (TCTA), etc.

The organic electroluminescence device 10 according to an embodiment of the present disclosure may include the above-described polycyclic compound in the emission layer EML between the first electrode EL1 and the second electrode EL2, thereby attaining a low driving voltage and high emission efficiency properties. The polycyclic compound according to an embodiment of the present disclosure may be a thermally activated delayed fluorescence dopant, and the emission layer EML may include the polycyclic compound to emit thermally activated delayed fluorescence, thereby attaining high emission efficiency properties.

The above-described polycyclic compound according to an embodiment of the present disclosure may be included in any organic layer in addition to the emission layer EML as a material for the organic electroluminescence device 10. For example, the organic electroluminescence device 10 according to an embodiment of the present disclosure may include the above-described polycyclic compound in at least one organic layer between the first electrode EL1 and the second electrode EL2, or in the capping layer on the second electrode EL2.

The above-described polycyclic compound according to an embodiment of the present disclosure includes a plurality of electron donors and an electron acceptor connecting the electron donors within the same molecule, thereby facilitating electron transfer in the molecule. Furthermore, the polycyclic compound according to an embodiment of the present disclosure has a dipole formed between the electron donors and electron acceptor, which increases a dipole moment in the molecule, and may be used as a luminescent material to improve emission efficiency.

The polycyclic compound according to an embodiment of the present disclosure includes an arylamine moiety, which fixes the electron acceptor to a planar conformation, and therefore, the wavelength half-width of light emitted from the emission layer including the polycyclic compound may be reduced. Accordingly, the organic electroluminescence device of an embodiment may be to emit light with high color purity, thereby attaining an improved display quality.

The polycyclic compound according to an embodiment of the present disclosure may be to emit thermally activated delayed fluorescence, thereby enhancing the emission efficiency of the organic electroluminescence device.

Hereinafter, the polycyclic compound according to an embodiment of the present disclosure and the organic electroluminescence device according to an embodiment of the present disclosure will be explained in more detail with reference to specific embodiments and comparative embodiments. The following embodiments are illustrated only for assisting the understanding of the present disclosure, and the scope of the present disclosure is not limited thereto.

EXAMPLES

1. Synthesis of Polycyclic Compound

The synthesis of polycyclic compound according to an embodiment of the present disclosure will be explained in more detail with reference to the exemplified synthetic methods of Compounds A-5, A-3, A-22 and A-24. However, the following synthetic methods are exemplary embodiments, and the synthetic method of the polycyclic compound according to an embodiment of the present disclosure is not limited thereto.

(1) Synthesis of Compound A-5

Compound A-5, a polycyclic compound according to an embodiment of the present disclosure, may be synthesized as shown in Reaction Scheme 1:

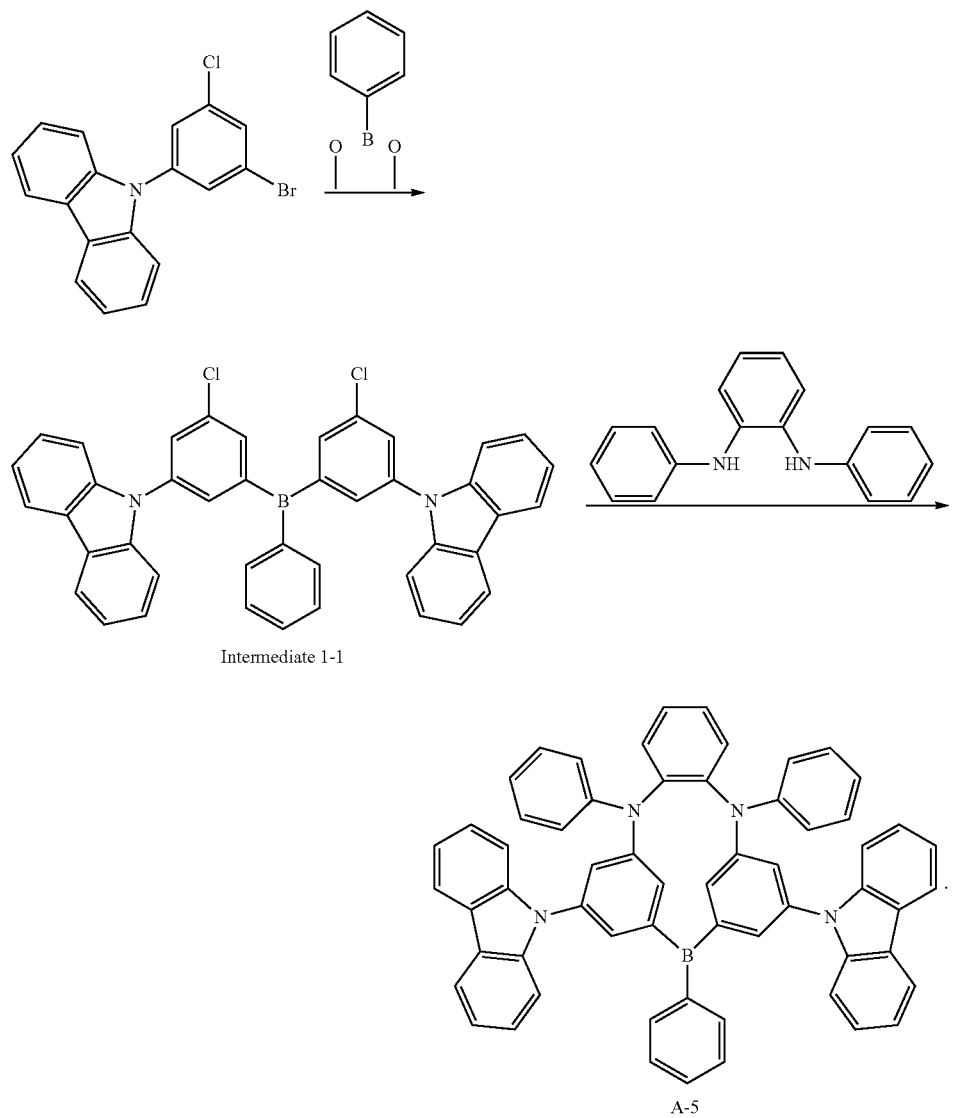

Synthesis of Intermediate 1-1

Dimethyl phenylboronate (1 eq) and 9-(3-bromo-5-chlorophenyl)-9H-carbazole (2.1 eq) were dissolved in toluene (500 mL). Pd(PPh$_3$)$_4$ (0.02 eq) was added thereto. Additionally, toluene (400 mL) and a saturated solution of 2 M K$_2$CO$_3$ (70 mL) were added thereto, and the mixture was stirred under reflux for about 5 hours. After the reaction was completed, the reactant was extracted and washed with methylene chloride (MC) (400 mL) and distilled water (150 mL), and then the solvent was removed. The solid thus obtained was purified by column chromatography to obtain Intermediate 1-1 (yield 55.4%). Intermediate 1-1 was identified by its molecular weight as measured by mass spectrometry. (HR-MS for C$_{42}$H$_{27}$BCl$_2$N$_2$ [M]+: calcd: 641, found: 640).

Synthesis of Compound A-5

Pd(dba)$_3$ (0.03 eq), (t-Bu)$_3$P (0.06 eq) and toluene (based on 0.1 M 1 eq reagent) were added to Intermediate 1-1 (1 eq) and N1,N2-diphenylbenzene-1,2-diamine (1 eq) in a flask, and the mixture was stirred under reflux for about 8 hours. After cooling to room temperature, the reactant was extracted with MC and washed with distilled water. The resultant was dried over MgSO$_4$, and distilled under reduced pressure. The residue was separated by column chromatography to obtain Compound A-5 (yield 78.87%). Compound A-5 was identified by its molecular weight as measured by mass spectrometry. (HR-MS for C$_{60}$H$_{41}$BN$_4$ [M]+: calcd: 828, found: 827).

(2) Synthesis of Compound A-3

Compound A-3, a polycyclic compound according to an embodiment of the present disclosure, may be synthesized as shown in Reaction Scheme 2:

Reaction Scheme 2

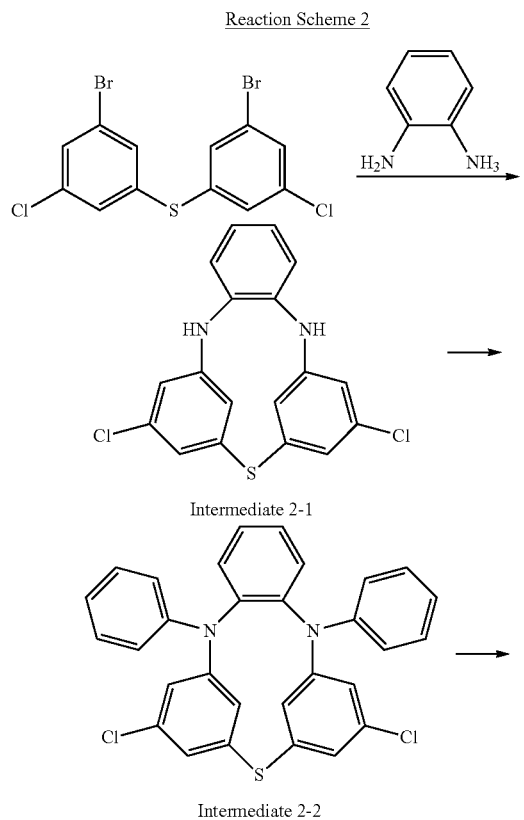

Intermediate 2-1

Intermediate 2-2

-continued

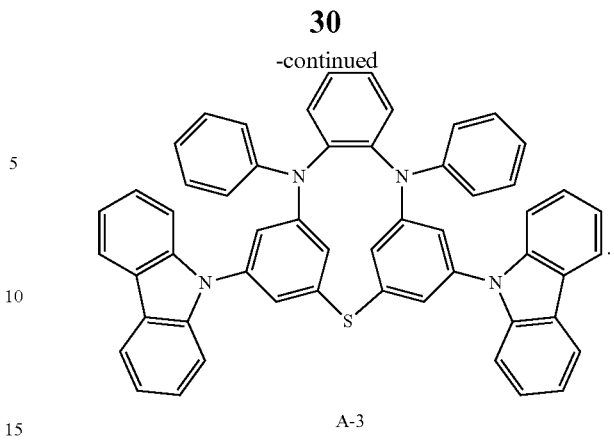

A-3

Synthesis of Intermediate 2-1

Pd(dba)$_3$ (0.03 eq), (t-Bu)$_3$P (0.06 eq) and toluene (based on 0.1 M 1 eq reagent) were added to benzene-1,2-diamine (1 eq) and bis(3-bromo-5-chlorophenyl)sulfane (1 eq), and the mixture was stirred under reflux for about 8 hours. After cooling to room temperature, the reactant was extracted with MC and washed with distilled water. The resultant was dried over MgSO$_4$, and distilled under reduced pressure. The residue was separated by column chromatography to obtain Intermediate 2-1 (yield 78.87%). Intermediate 2-1 was identified by its molecular weight as measured by mass spectrometry. (HR-MS for C$_{18}$H$_{12}$Cl$_2$N$_2$S [M]+: calcd: 359, found: 358).

Synthesis of Intermediate 2-2

Pd(dba)$_3$ (0.03 eq), (t-Bu)$_3$P (0.06 eq), and toluene (based on 0.1 M 1 eq reagent) were added to Intermediate 2-1 (1 eq) and bromobenzene (2.2 eq), and the mixture was stirred under reflux for about 8 hours. After cooling to room temperature, the reactant was extracted with MC and washed with distilled water. The resultant was dried over MgSO$_4$, and distilled under reduced pressure. The residue was separated by column chromatography to obtain Intermediate 2-2 (yield 87%). Intermediate 2-2 was identified by its molecular weight as measured by mass spectrometry. (HR-MS for C$_{30}$H$_{20}$Cl$_2$N$_2$S [M]+: calcd: 512, found: 511).

Synthesis of Compound A-3

Pd(dba)$_3$ (0.03 eq), (t-Bu)$_3$P (0.06 eq) and toluene (based on 0.1 M 1 eq reagent) were added to Intermediate 2-2 (1 eq) and carbazole (2.2 eq) in a flask, and the mixture was stirred under reflux for about 8 hours. After cooling to room temperature, the reactant was extracted with MC and washed with distilled water. The resultant was dried over MgSO$_4$, and distilled under reduced pressure. The residue was separated by column chromatography to obtain Compound A-3 (yield 88.44%). Compound A-3 was identified by its molecular weight as measured by mass spectrometry. (HR-MS for C$_{54}$H$_{36}$N$_4$S [M]+: calcd: 772, found: 771).

(3) Synthesis of Compound A-22

Compound A-22, a polycyclic compound according to an embodiment of the present disclosure, may be synthesized as shown in Reaction Scheme 3:

Reaction Scheme 3

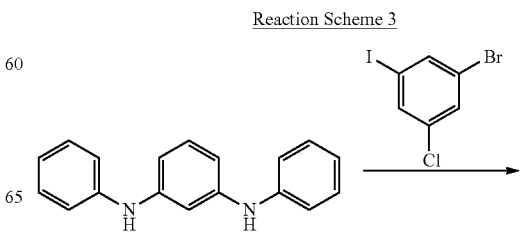

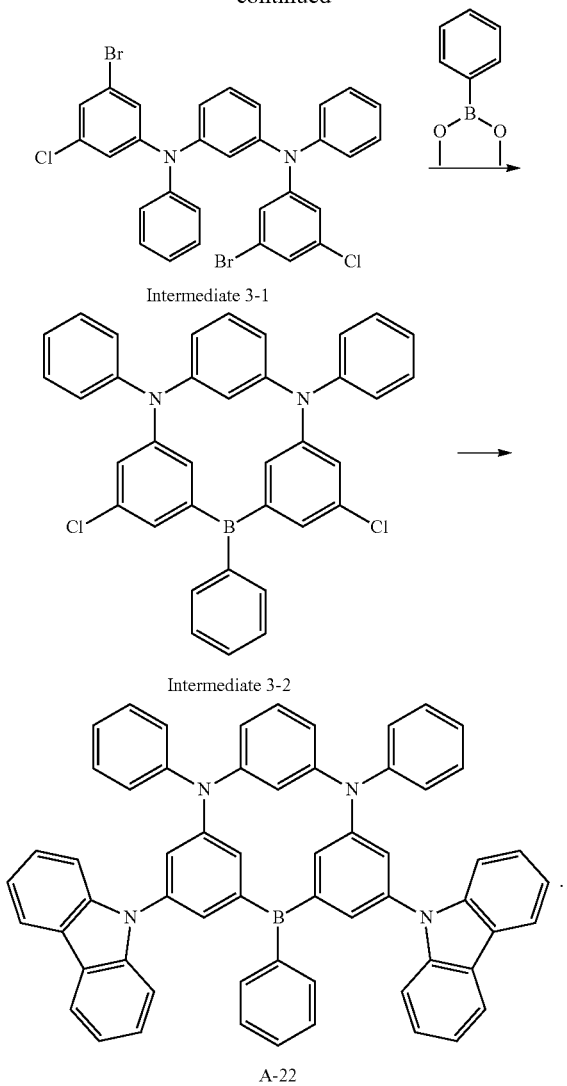

Synthesis of Intermediate 3-1

Pd(dba)₃ (0.03 eq), (t-Bu)₃P (0.06 eq) and toluene (based on 0.1 M 1 eq reagent) were added to N1,N3-diphenylbenzene-1,3-diamine (1 eq) and 1-bromo-3-chloro-5-iodobenzene (2.1 eq), and the mixture was stirred at about 120° C. for about 3 hours. After cooling to room temperature, the reactant was extracted with MC and washed with distilled water. The resultant was dried over MgSO₄, and distilled under reduced pressure. The residue was separated by column chromatography to obtain Intermediate 3-1 (yield 81.7%). Intermediate 3-1 was identified by its molecular weight as measured by mass spectrometry. (HR-MS for $C_{30}H_{20}Br_2Cl_2N_2$ [M]+: calcd: 639, found: 638).

Synthesis of Intermediate 3-2

Intermediate 3-1 (1 eq) and dimethyl phenylboronate (1 eq) were dissolved in toluene (500 mL). Pd(PPh₃)₄ (0.02 eq) was added thereto. Additionally, toluene (400 mL) and a saturated solution of 2 M K₂CO₃ (70 mL) were added thereto, and the mixture was stirred under reflux for about 5 hours. After the reaction was complete, the reactant was extracted and washed with MC (400 mL) and distilled water (150 mL), and the solvent was removed. The solid thus obtained was purified by column chromatography to obtain Intermediate 3-2 (yield 66.7%). Intermediate 3-2 was identified by its molecular weight as measured by mass spectrometry. (HR-MS for $C_{36}H_{25}BCl_2N_2$ [M]+: calcd: 567, found: 566).

Synthesis of Compound A-22

Pd(dba)₃ (0.03 eq), (t-Bu)₃P (0.06 eq) and toluene (based on 0.1 M 1 eq reagent) were added to Intermediate 3-2 (1 eq) and carbazole (2.2 eq) in a flask, and the mixture was stirred under reflux for about 8 hours. After cooling to room temperature, the reactant was extracted with MC and washed with distilled water. The resultant was dried over MgSO₄, and distilled under reduced pressure. The residue was separated by column chromatography to obtain Compound A-22 (yield 85.6%). Compound A-22 was identified by its molecular weight as measured by mass spectrometry. (HR-MS for $C_{60}H_{41}BN_4$ [M]+: calcd: 828, found: 827).

(4) Synthesis of Compound A-24

Compound A-24 was synthesized using substantially the same synthetic method for Compound A-5, except for using N1,N2-diphenylbenzene-1,3-diamine instead of N1,N3-diphenylbenzene-1,2-diamine, and using 3-bromo-5-chloro-N,N-diphenylaniline instead of 9-(3-bromo-5-chlorophenyl)-9H-carbazole in Reaction Scheme 1. Compound A-24 was identified by its molecular weight as measured by mass spectrometry. (HR-MS for $C_{60}H_{45}BN_4$ [M]+: calcd: 832, found: 827)

2. Evaluation of Energy Level of Compound

Table 1 shows the HOMO energy level, the LUMO energy level, the lowest singlet excitation energy level (S1 level), the lowest triplet excitation energy level (T1 level), and $\Delta E_{ST}$ value of Example Compounds A-5, A-3, A-22 and A-24.

The energy level values in Table 1 were calculated using an ab initio molecular orbital method, specifically, using the B3LYP/6-31 G (d) hybrid functional under Gaussian09 (Gaussian, Inc.). $\Delta E_{ST}$ is the difference between the lowest singlet energy level (S1 level) and the lowest triplet energy level (T1 level).

TABLE 1

| Compounds | HOMO (eV) | LUMO (eV) | S1 (eV) | T1 (eV) | $\Delta E_{ST}$ (eV) |
|---|---|---|---|---|---|
| Compound A-5 | −5.26 | −2.315 | 2.87 | 2.72 | 0.08 |
| Compound A-9 | −5.685 | −2.775 | 2.87 | 2.65 | 0.03 |
| Compound A-10 | −5.63 | −2.560 | 2.73 | 2.73 | 0.13 |
| Compound A-24 | −5.61 | −2.455 | 3.05 | 2.79 | 0.15 |

Example Compounds A-5, A-3, A-22 and A-24 each have an $\Delta E_{ST}$ of about 0.2 eV or less. Accordingly, Example Compounds A-5, A-3, A-22 and A-24 may each be used as a dopant material for thermally activated delayed fluorescence.

3. Manufacturing of Organic Electroluminescence Devices Including Polycyclic Compounds and Evaluation Thereof Manufacturing of Organic Electroluminescence Devices The organic electroluminescence devices including the polycyclic compounds according to an embodiment of the present disclosure were manufactured by the following method. The organic electroluminescence devices of Examples 1 to 4 were manufactured using the above Compounds A-5, A-3, A-22, and A-24 as dopant materials in emission layers of the respective devices.

The organic electroluminescent device of Comparative Example 1 was manufactured using BH1 as a host material and BD1 as a dopant material. The organic electroluminescent device of Comparative Example 2 was manufactured using Comparative Compound C1 as a dopant material in an emission layer.
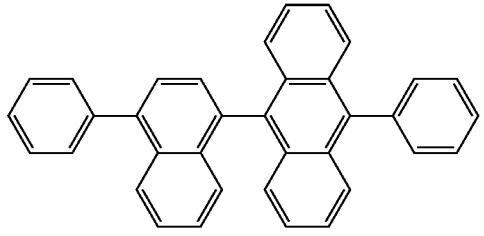
BH1
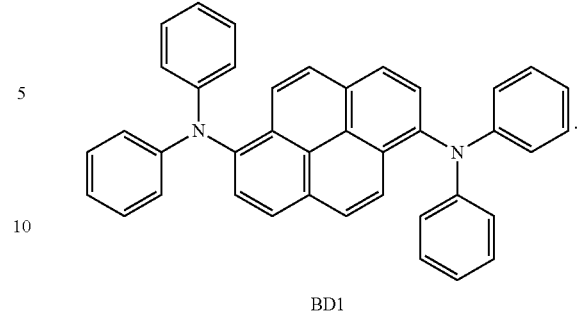
BD1
The compounds used in Examples 1 to 4 and Comparative Example 2 are shown in Table 2.
TABLE 2
| Compound A-5 | 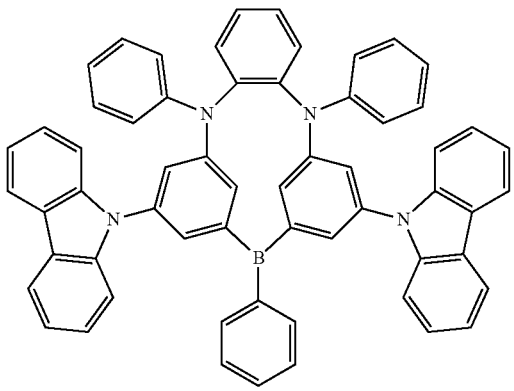 [SMILES: c1ccc(B2c3cc(cc(-n4c5ccccc5c5ccccc54)c3)N(c3ccccc3)c3ccccc3N(c3ccccc3)c3cc2cc(-n2c4ccccc4c4ccccc42)c3)cc1] A-5 |
| --- | --- |
| Compound A-3 | 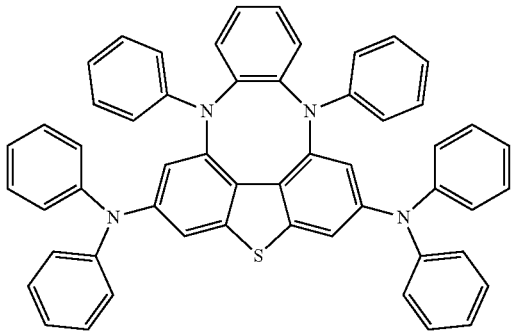 [SMILES: c1ccc(N(c2ccccc2)c2cc3sc4cc(N(c5ccccc5)c5ccccc5)cc5c4c3c(c2)n(-c2ccccc2)c2ccccc2n5-c2ccccc2)cc1] A-9 |
| Compound A-22 | 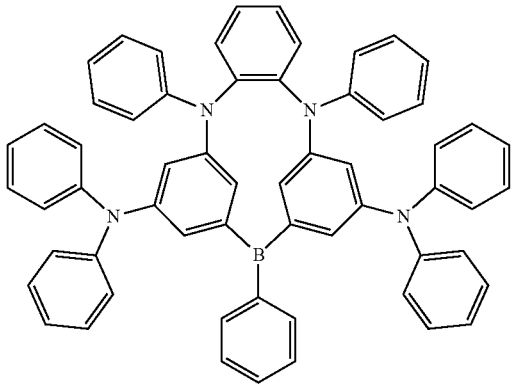 [SMILES: c1ccc(B2c3cc(N(c4ccccc4)c4ccccc4)cc(c3)N(c3ccccc3)c3ccccc3N(c3ccccc3)c3cc2cc(N(c2ccccc2)c2ccccc2)c3)cc1] A-10 |

TABLE 2-continued

| Compound A-24 | 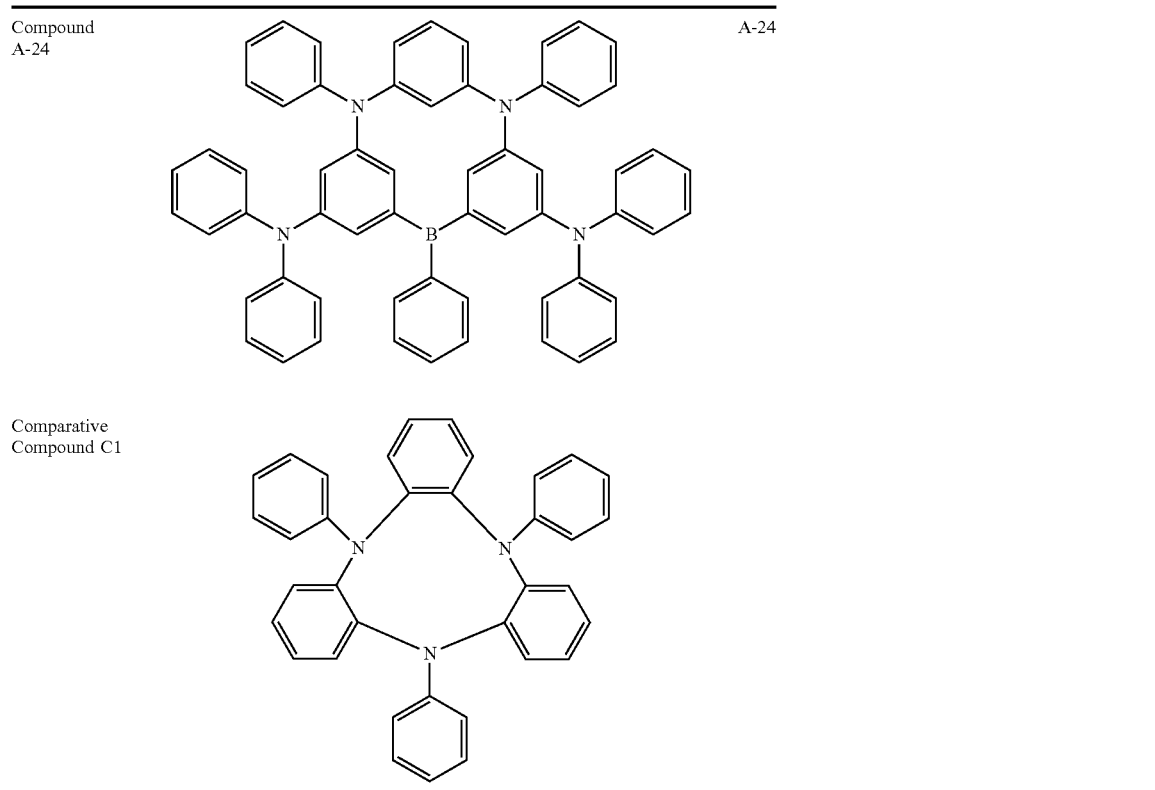 | A-24 |
|---|---|---|
| Comparative Compound C1 | | |

On a glass substrate, ITO with a thickness of about 1,200 Å was patterned to form a first electrode, which was washed with isopropyl alcohol and ultrapure water and cleaned with ultrasonic waves, exposed to UV for about 30 minutes, and treated with ozone. Then, NPB was deposited to a thickness of about 40 Å to form a hole injection layer, and mCP was deposited to a thickness of about 10 Å to form a hole transport layer.

On the hole transport layer, mCBP and the polycyclic compound according to an embodiment of the present disclosure (e.g., in the Examples), or Comparative Compound C1 (e.g. in Comparative Example 2), were co-deposited at a ratio of 85:15 to form an emission layer with a thickness of about 200 Å. For example, in Examples 1 to 4, each of Compounds A-5, A-9, A-10 and A-24 was respectively mixed with mCBP and co-deposited to form an emission layer, and in Comparative Example 2, Comparative Compound C1 mixed with mCBP was co-deposited to form an emission layer.

On the emission layer, an electron transport layer was formed using ETL1 to a thickness of about 300 Å, and a second electrode was formed using aluminum (Al) to a thickness of about 1,200 Å.

The materials used for the manufacture of the organic electroluminescence devices of Examples and Comparative Examples are shown below.

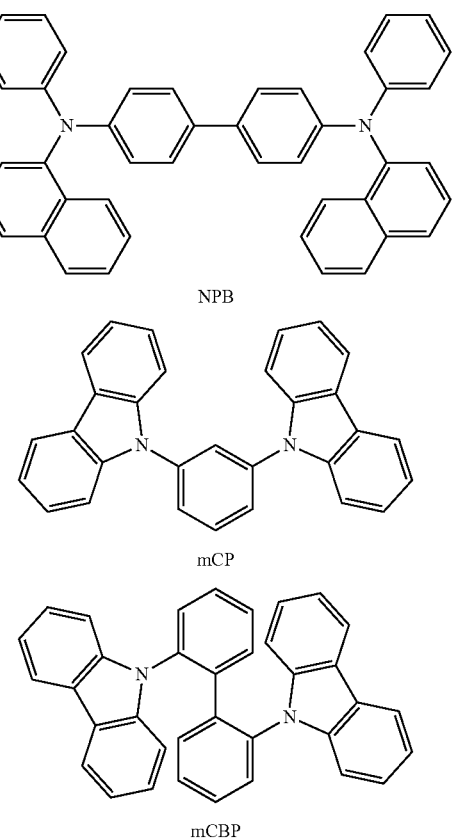

NPB mCP mCBP

-continued

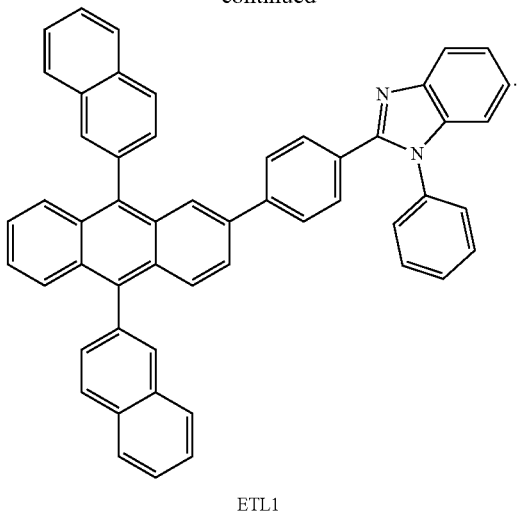

ETL1

Property Evaluation of Organic Electroluminescence Devices

The evaluation results of the organic electroluminescence devices of Examples 1 to 4 and Comparative Examples 1 and 2 are shown in Table 3. Table 3 shows the driving voltage, emission efficiency, and external quantum efficiency (EQE) for the organic electroluminescence devices manufactured in the Examples and Comparative Examples. In the property evaluation results of Table 3, the emission efficiency was a current efficiency value at a current density of 10 mA/cm$^2$.

TABLE 3

| Device manufacturing examples | Dopant material of emission layer | Driving voltage (V) | Emission efficiency (cd/A) | EQE (%) |
|---|---|---|---|---|
| Example 1 | Compound A-4 | 4.7 | 16.4 | 6.9 |
| Example 2 | Compound A-9 | 4.4 | 17.1 | 6.78 |
| Example 3 | Compound A-10 | 5.2 | 16.7 | 6.98 |
| Example 4 | Compound A-24 | 4.9 | 19.54 | 7.0 |
| Comparative Example 1 | BD1 | 7.44 | 4.84 | 2.99 |
| Comparative Example 2 | Comparative Compound C1 | 5.5 | 13.7 | 6.7 |

Referring to the results in Table 3, it may be found that each of the organic electroluminescence devices of Examples 1 to 4 using the polycyclic compound as a material for an emission layer have a low driving voltage, high emission efficiency and high external quantum efficiency compared to the Comparative Examples.

The organic electroluminescence devices of Examples 1 to 4 showed enhanced emission efficiency compared to the organic electroluminescence device of Comparative Example 1 including BD1 (a typical fluorescent dopant material), in the emission layer. Accordingly, it may be found that the polycyclic compounds used in Examples emit thermally activated delayed fluorescence.

For example, compared with the dopant compound used in Comparative Example 1, the polycyclic compounds according to an embodiment of the present disclosure used in Examples 1 to 4, which include both the electron donor and electron acceptor in one compound unit, may be to emit delayed fluorescence, thereby attaining high device efficiency. Meanwhile, the organic electroluminescence device of Comparative Example 2 used the same host material as in Examples 1 to 4, but with Comparative Compound C1 as a dopant. Comparative Compound C1 has a structure different from the polycyclic compounds including a plurality of electron donors and an electron acceptor connecting the electron donors, and the organic electroluminescence device of Comparative Example 2 appears to show a high driving voltage, low emission efficiency, and low external quantum efficiency compared to the Examples. For example, the polycyclic compounds used in the Examples may enable enhanced device efficiency with low driving voltage, compared to dopant compounds such as those used in the Comparative Examples.

The organic electroluminescence device according to an embodiment of the present disclosure may attain improved device properties, including a low driving voltage and high efficiency.

The polycyclic compound according to an embodiment of the present disclosure may be included in an emission layer of an organic electroluminescence device, thereby contributing to high efficiency of the device.

Although the exemplary embodiments of the present disclosure have been described, it is understood that the present disclosure should not be limited to these exemplary embodiments, but various changes and modifications can be made by one ordinary skilled in the art within the spirit and scope of the present disclosure as hereinafter claimed.

As used herein, the terms "use", "using", and "used" may be considered synonymous with the terms "utilize", "utilizing", and "utilized", respectively. Further, the use of "may" when describing embodiments of the present disclosure refers to "one or more embodiments of the present disclosure".

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Accordingly, the scope of the present disclosure is to be determined by the broadest permissible interpretation of the following claims and their equivalents, and shall not be restricted or limited by the foregoing detailed description.

What is claimed is:

1. An organic electroluminescence device, comprising:
   a first electrode;
   a hole transport region on the first electrode;
   an emission layer on the hole transport region, the emission layer comprising a polycyclic compound represented by Formula 1;
   an electron transport region on the emission layer; and
   a second electrode on the electron transport region, wherein the first electrode and the second electrode each independently comprise at least one selected from the group consisting of Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, or an oxide thereof:

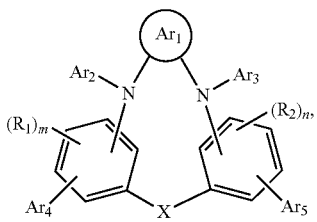

Formula 1 wherein in Formula 1,

X is S, O, C(=O), $NR_a$, or $BR_b$, $R_1$, $R_2$, $R_a$, and $R_b$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 5 to 30 carbon atoms for forming a ring, and $R_1$, $R_2$, $R_a$, and $R_b$ optionally form a ring by combining adjacent groups with each other, m and n are each independently an integer of 0 to 3, $Ar_1$ is an unsubstituted phenylene group, $Ar_2$ and $Ar_3$ are each independently a hydrocarbon ring having 5 to 60 carbon atoms for forming a ring, or a heterocycle having 5 to 60 carbon atoms for forming a ring, in which no nitrogen atom is comprised in the ring, and $Ar_4$ and $Ar_5$ are each independently represented by Formula 2:

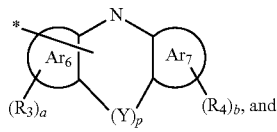

Formula 2 wherein in Formula 2, p is 0 or 1, when p is 1, Y is a direct linkage or $CR_cR_d$, $Ar_6$ and $Ar_7$ are each independently a hydrocarbon ring having 5 to 60 carbon atoms for forming a ring, or a heterocycle having 5 to 60 carbon atoms for forming a ring which comprises no nitrogen atom for forming a ring, $R_3$, $R_4$, $R_c$, and $R_d$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 5 to 30 carbon atoms for forming a ring, and $R_3$, $R_4$, $R_c$, and $R_d$ optionally form a ring by combining adjacent groups with each other, and a and b are each independently an integer of 0 to 4.

2. The organic electroluminescence device of claim 1, wherein the emission layer is configured to emit a delayed fluorescence.

3. The organic electroluminescence device of claim 1, wherein the emission layer is a delayed fluorescence emission layer comprising a host and a dopant, and the dopant comprises the polycyclic compound represented by Formula 1.

4. The organic electroluminescence device of claim 1, wherein the emission layer is configured to emit blue light.

5. The organic electroluminescence device of claim 1, wherein the emission layer is provided by an inkjet process.

6. The organic electroluminescence device of claim 1, wherein Formula 1 is represented by Formula 1-1:

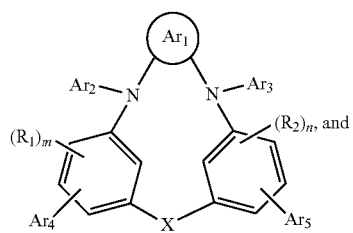

Formula 1-1 wherein in Formula 1-1,

X, $Ar_1$ to $Ar_5$, $R_1$, $R_2$, m, and n are the same as defined in connection with Formula 1.

7. The organic electroluminescence device of claim 1, wherein Formula 1 is represented by Formula 1-2A or 1-2B:

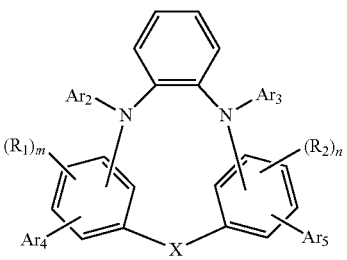

Formula 1-2A

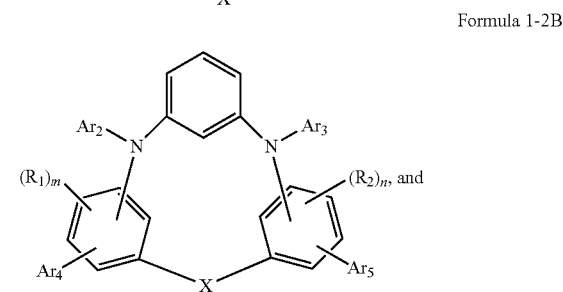

Formula 1-2B wherein in Formulae 1-2A and 1-2B,

X, $Ar_2$ to $Ar_5$, $R_1$, $R_2$, m, and n are the same as defined in connection with Formula 1.

8. The organic electroluminescence device of claim 1, wherein Formula 1 is represented by Formula 1-3A or 1-3B:

Formula 1-3A

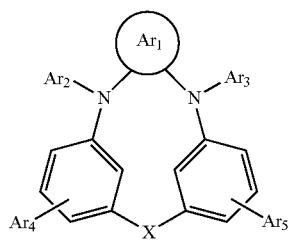

Formula 1-3B

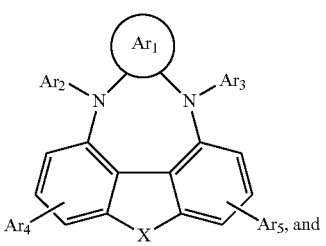

wherein in Formulae 1-3A and 1-3B,
X, and Ar₁ to Ar₅ are the same as defined in connection with Formula 1.

9. The organic electroluminescence device of claim 1, wherein Formula 2 is represented by Formula 2-1 or 2-2:

Formula 2-1

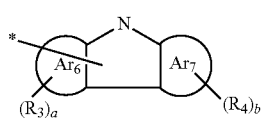

Formula 2-2

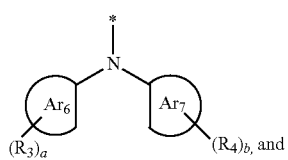

wherein in Formulae 2-1 and 2-2,
Ar₆, Ar₇, R₃, R₄, a, and b are the same as defined in connection with Formula 2.

10. The organic electroluminescence device of claim 1, wherein the polycyclic compound represented by Formula 1 comprises at least one compound selected from Compound Group 1:

Compound Group 1

A-1

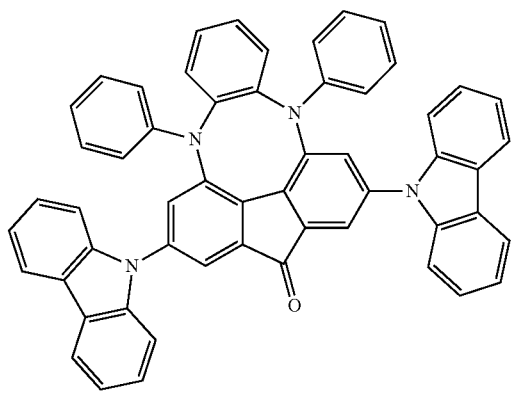

A-2

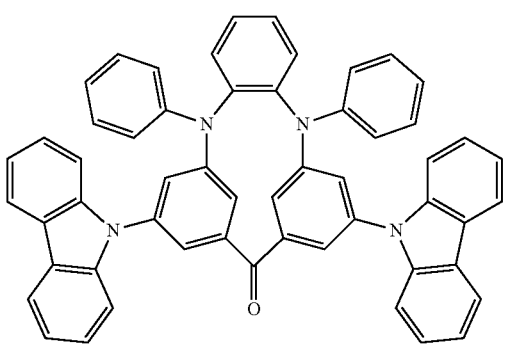

A-3

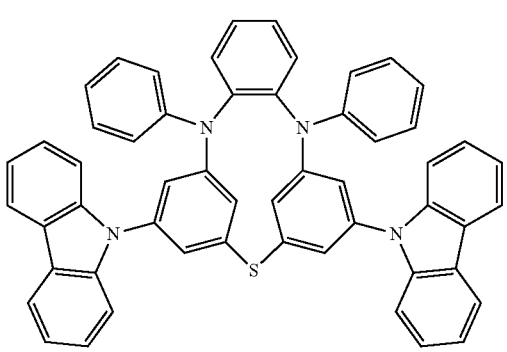

A-4

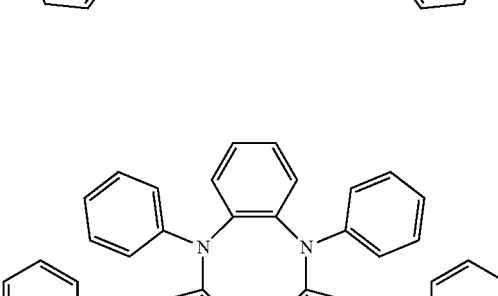

A-5

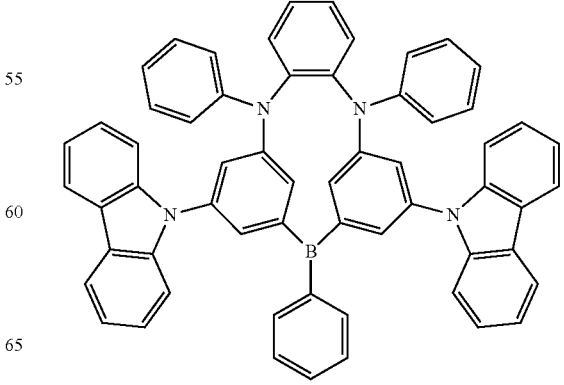

A-6
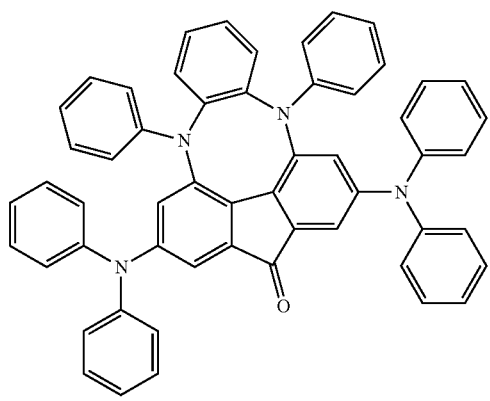
A-10
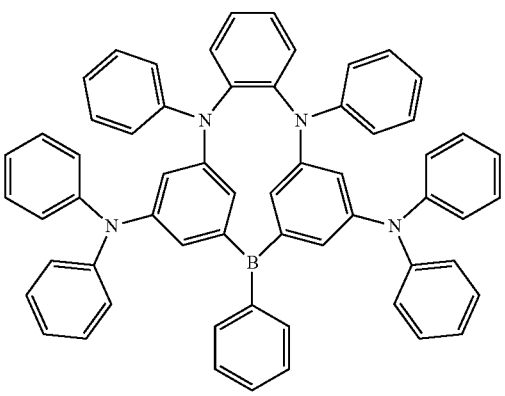
A-7
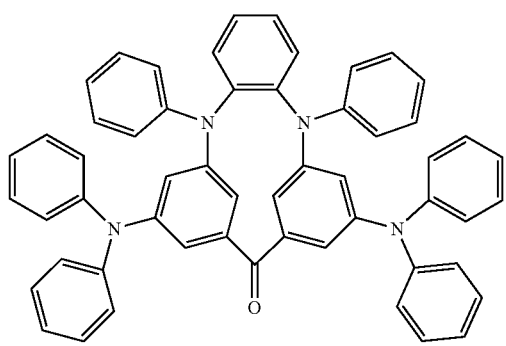
A-11
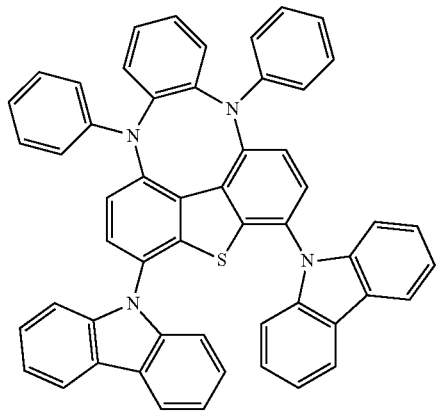
A-8
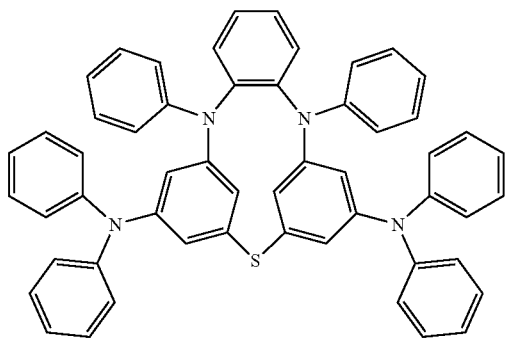
A-12
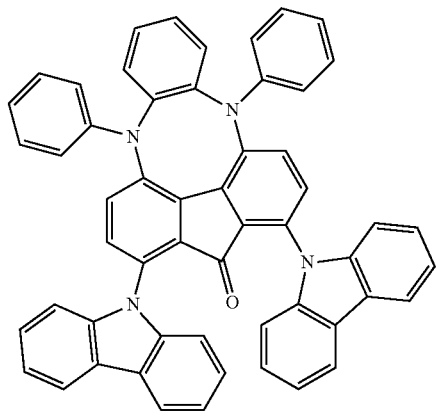
A-9
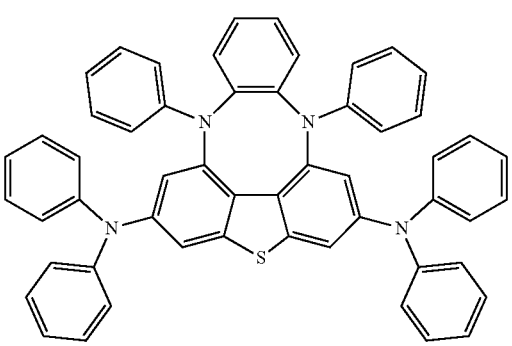
A-13
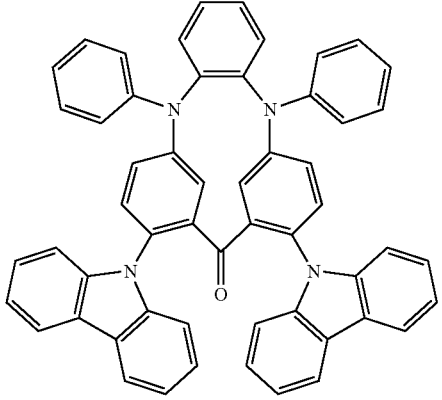

A-14
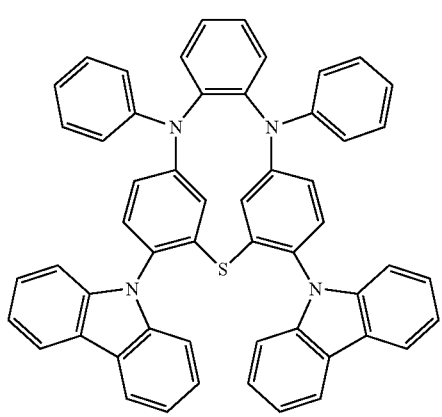
A-18
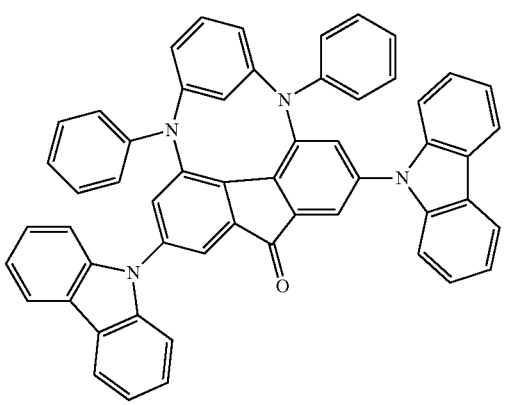
A-15
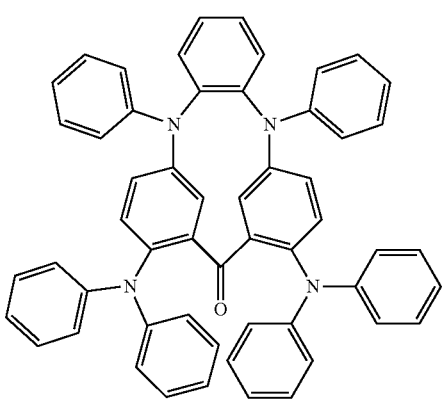
A-19
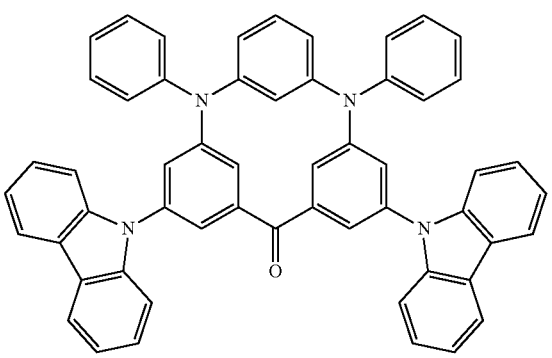
A-16
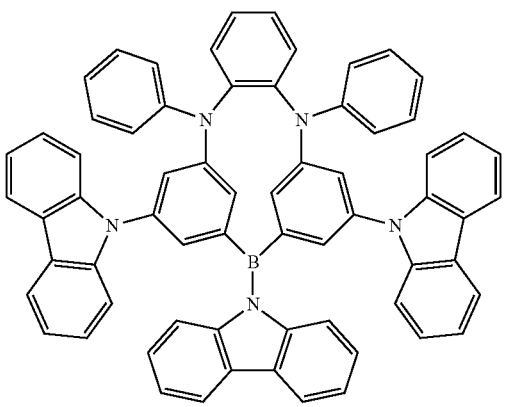
A-20
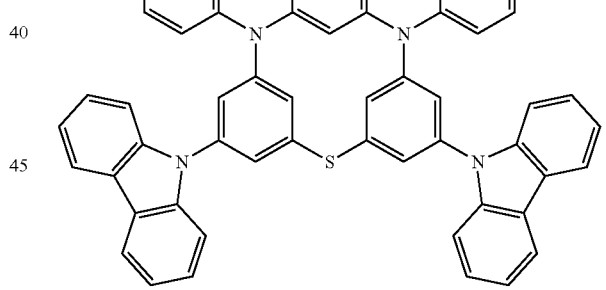
A-17
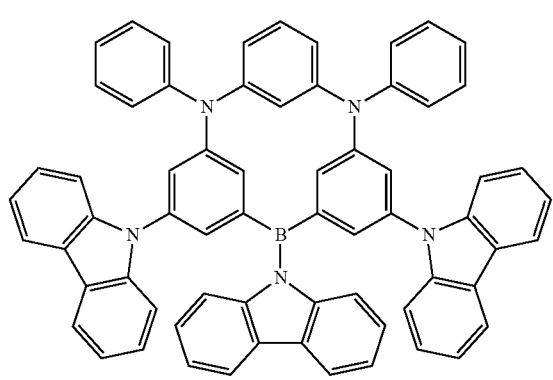
A-21
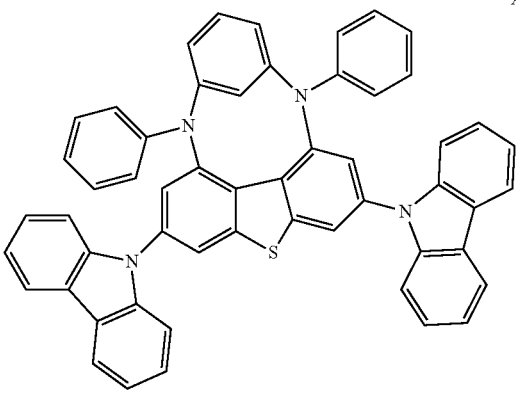

-continued

A-22
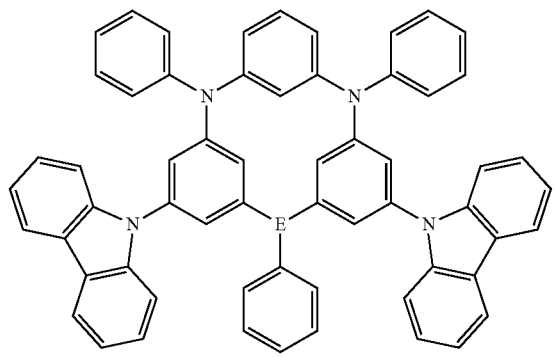

A-23
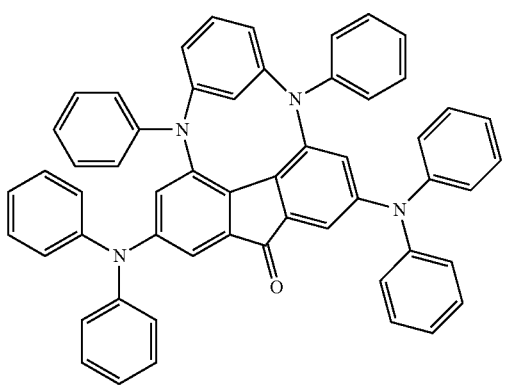

A-24
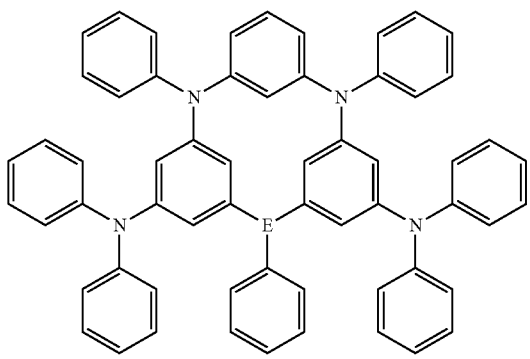 [SMILES: c1ccc(B2c3cc(N(c4ccccc4)c4ccccc4)cc(c3)N(c3ccccc3)c3cccc(c3)N(c3ccccc3)c3cc2cc(N(c2ccccc2)c2ccccc2)c3)cc1]

A-25
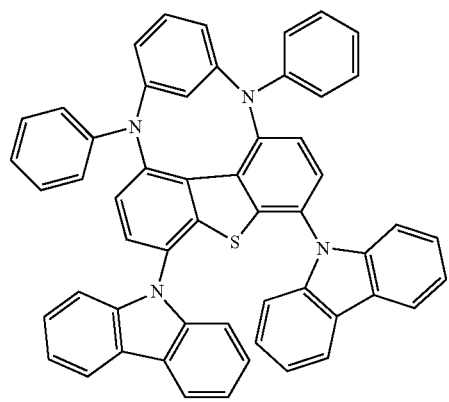

-continued

A-26
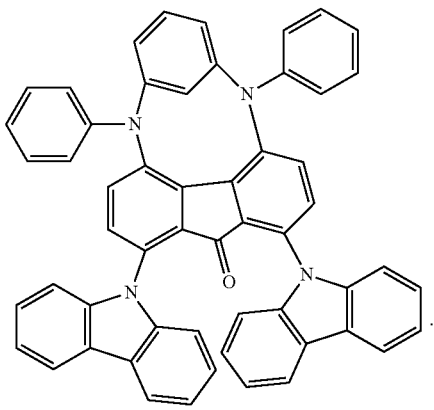

11. A polycyclic compound represented by Formula 1:

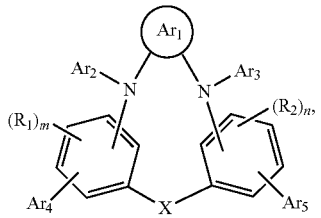

Formula 1 wherein in Formula 1,

X is S, O, C(=O), NR$_a$, or BR$_b$,

R$_1$, R$_2$, R$_a$, and R$_b$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 5 to 30 carbon atoms for forming a ring, and R$_1$, R$_2$, R$_a$, and R$_b$ optionally form a ring by combining adjacent groups with each other, m and n are each independently an integer of 0 to 3, Ar$_1$ is an unsubstituted phenylene group, Ar$_2$ and Ar$_3$ are each independently a hydrocarbon ring having 5 to 60 carbon atoms for forming a ring, or a heterocycle having 5 to 60 carbon atoms for forming a ring, in which no nitrogen atom is comprised in the ring, and Ar$_4$ and Ar$_5$ are each independently represented by Formula 2:

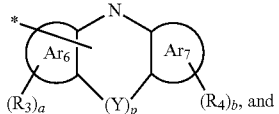

Formula 2 wherein in Formula 2, p is 0 or 1, when p is 1, Y is a direct linkage or CR$_c$R$_d$, Ar$_6$ and Ar$_7$ are each independently a hydrocarbon ring having 5 to 60 carbon atoms for forming a ring, or a heterocycle having 5 to 60 carbon atoms for forming a ring, in which no nitrogen atom is comprised in the ring, $R_3$, $R_4$, $R_c$, and $R_d$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, or a substituted or unsubstituted heteroaryl group having 5 to 30 carbon atoms for forming a ring, and $R_3$, $R_4$, $R_c$, and $R_d$ optionally form a ring by combining adjacent groups with each other, and a and b are each independently an integer of 0 to 4.

12. The polycyclic compound of claim 11, wherein Formula 1 is represented by Formula 1-1:

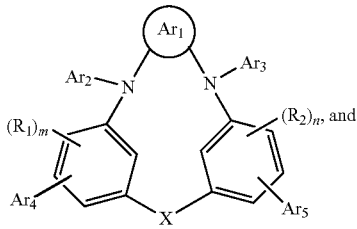

Formula 1-1 wherein in Formula 1-1,

X, $Ar_1$ to $Ar_5$, $R_1$, $R_2$, m, and n are the same as defined in connection with Formula 1.

13. The polycyclic compound of claim 11, wherein Formula 1 is represented by Formula 1-2A or 1-2B:

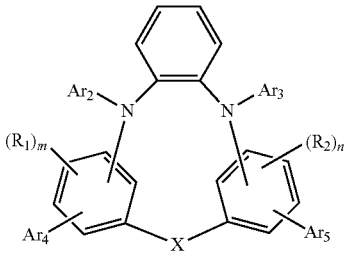

Formula 1-2A

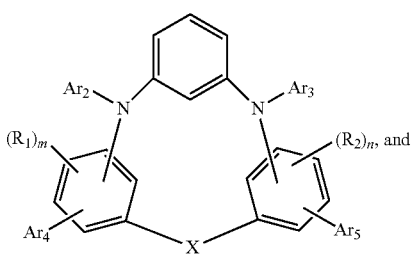

Formula 1-2B wherein in Formulae 1-2A and 1-2B,

X, $Ar_2$ to $Ar_5$, $R_1$, $R_2$, m, and n are the same as defined in connection with Formula 1.

14. The polycyclic compound of claim 11, wherein Formula 1 is represented by Formula 1-3A or 1-3B:

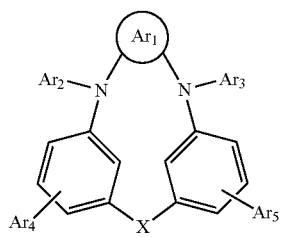

Formula 1-3A

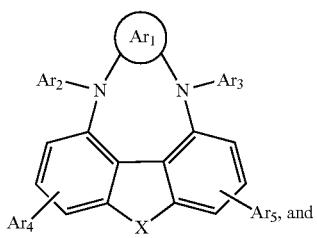

Formula 1-3B wherein in Formulae 1-3A and 1-3B,

X, and $Ar_1$ to $Ar_5$ are the same as defined in connection with Formula 1.

15. The polycyclic compound of claim 11, wherein Formula 2 is represented by Formula 2-1 or 2-2:

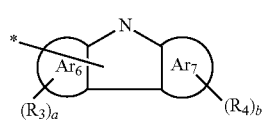

Formula 2-1

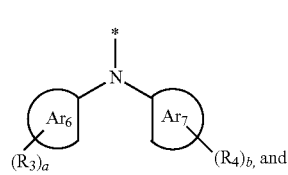

Formula 2-2 wherein in Formulae 2-1 and 2-2, $Ar_6$, $Ar_7$, $R_3$, $R_4$, a, and b are the same as defined in connection with Formula 2.

16. The polycyclic compound of claim 11, wherein $Ar_2$ and $Ar_3$ are each independently a substituted or unsubstituted phenyl group.

17. The polycyclic compound of claim 11, wherein $Ar_4$ and $Ar_5$ are the same as each other.

18. The polycyclic compound of claim 11, wherein the polycyclic compound represented by Formula 1 is a thermally activated delayed fluorescence material.

19. The polycyclic compound of claim 11, wherein the polycyclic compound represented by Formula 1 is at least one compound selected from Compound Group 1:

Compound Group 1
A-1
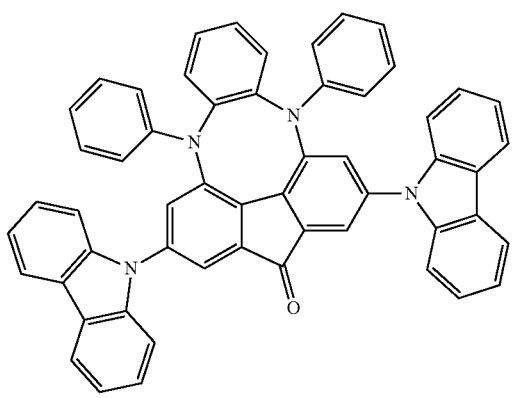
A-2
A-3
A-4
A-5
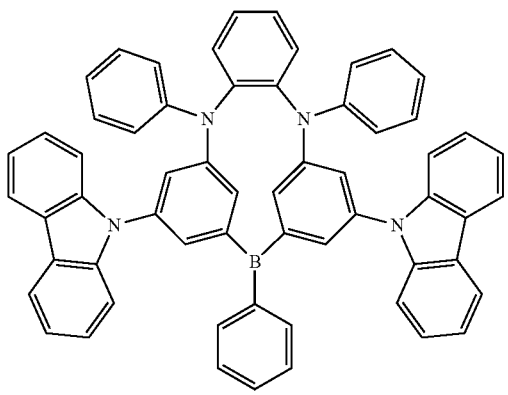
A-6
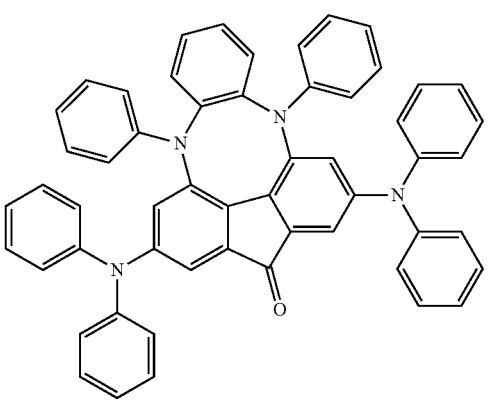
A-7
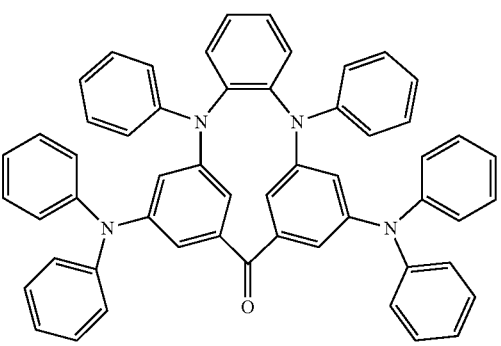
A-8
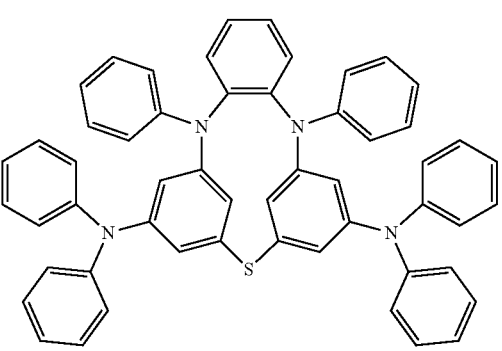

A-9
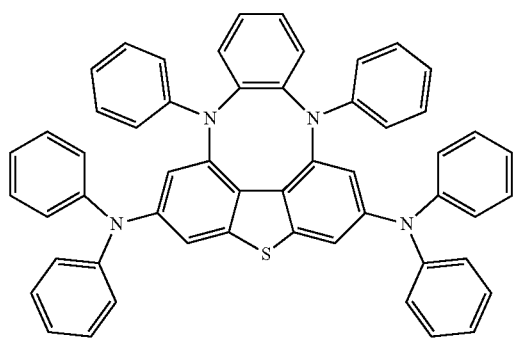
A-10
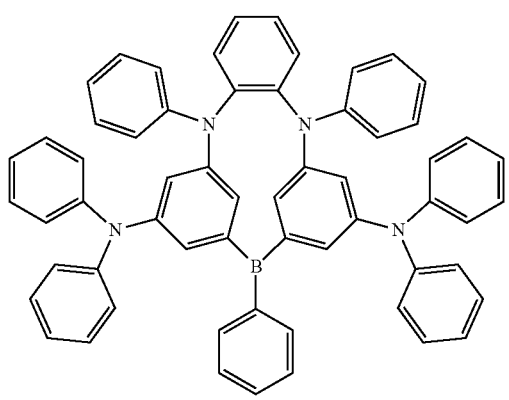
A-11
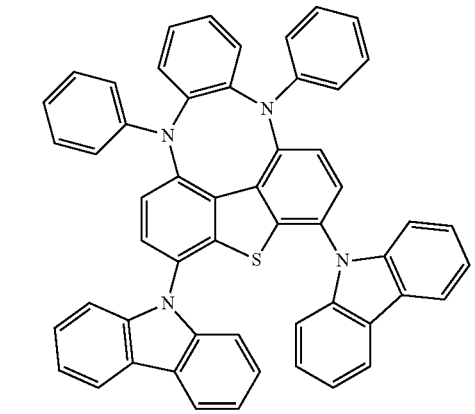
A-12
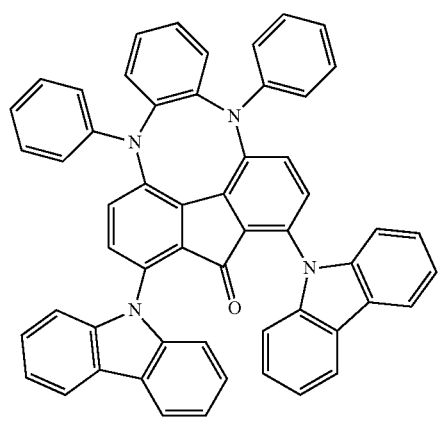
A-13
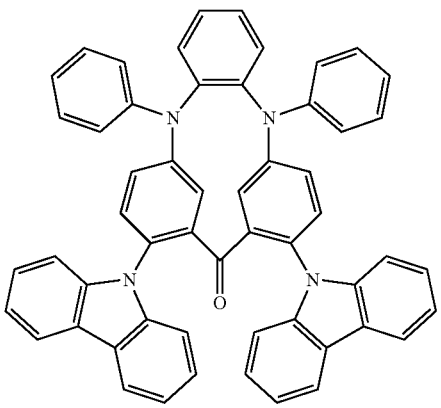
A-14
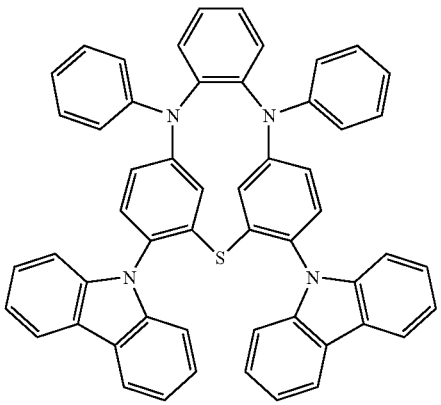
A-15
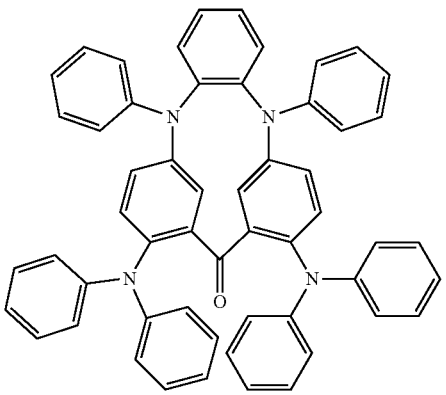
A-16
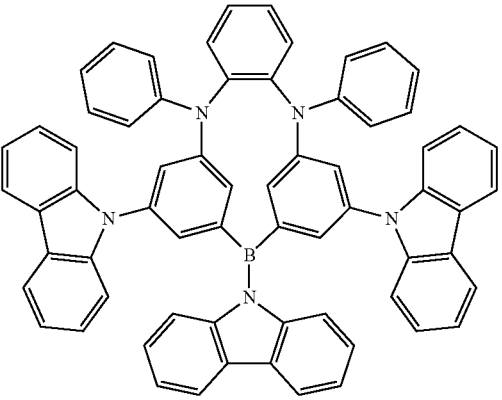

A-17
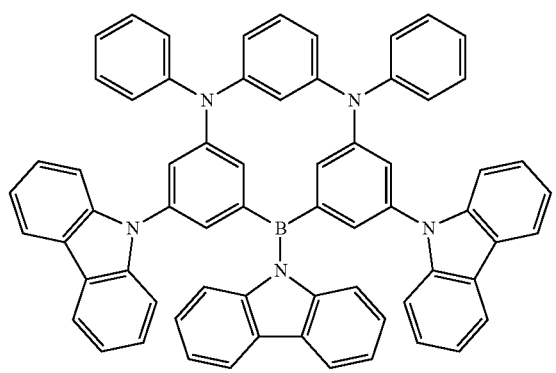
A-18
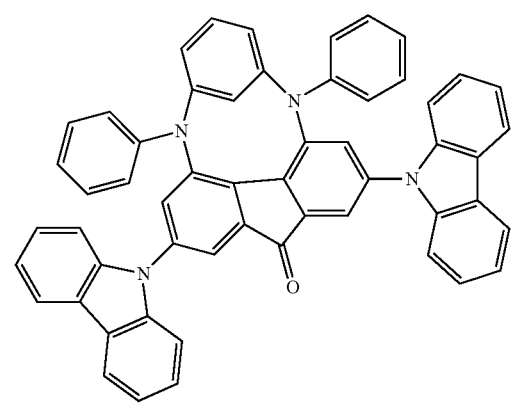
A-19
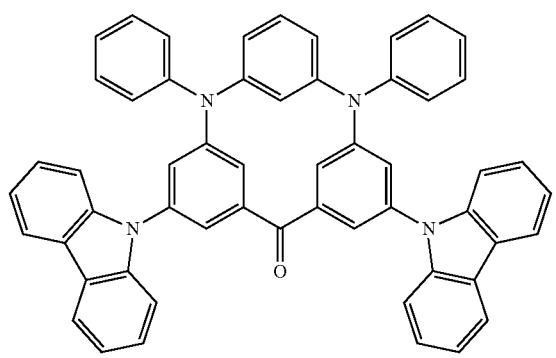
A-20
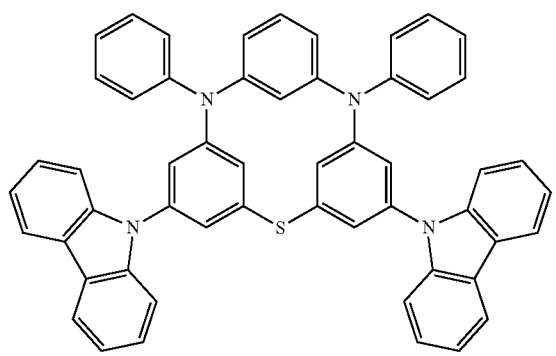
A-21
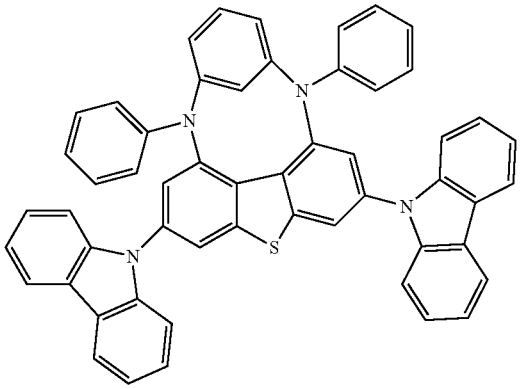
A-22
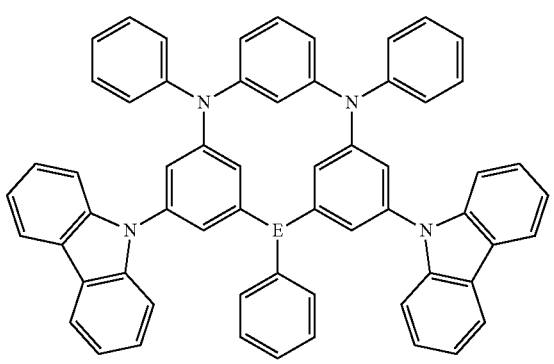
A-23
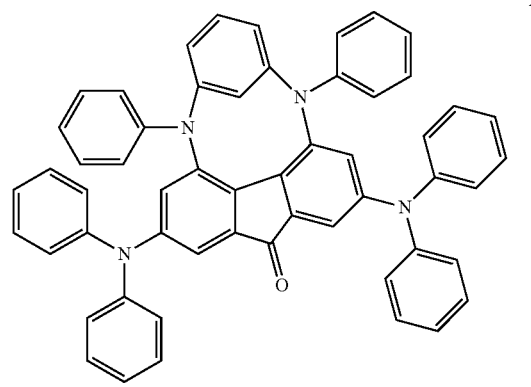
A-24
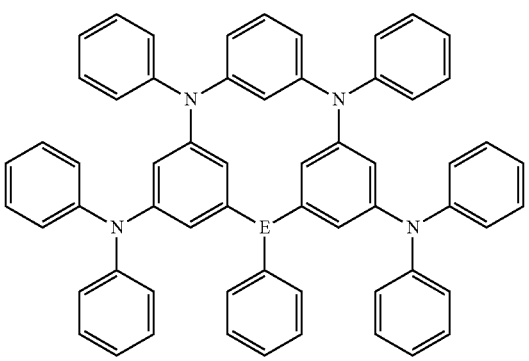

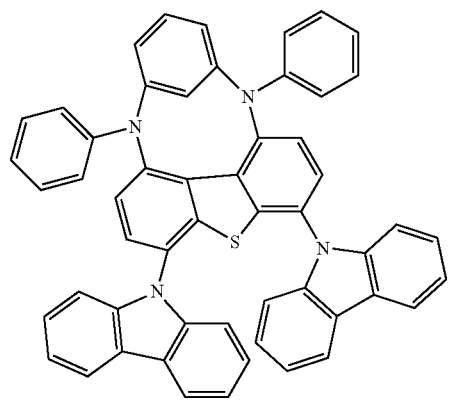
A-25
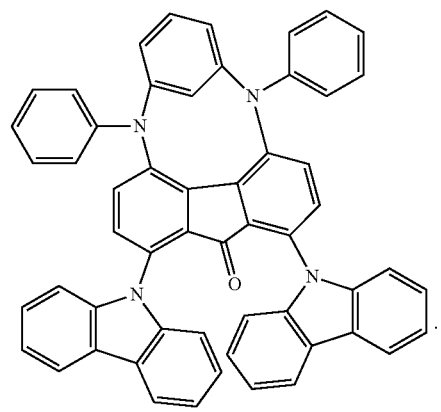
A-26
* * * * *

UNITED STATES PATENT AND TRADEMARK OFFICE
CERTIFICATE OF CORRECTION

| | | |
|---|---|---|
| PATENT NO. | : 11,335,862 B2 | Page 1 of 3 |
| APPLICATION NO. | : 16/575109 | |
| DATED | : May 17, 2022 | |
| INVENTOR(S) | : Jungsub Lee et al. | |

It is certified that error appears in the above-identified patent and that said Letters Patent is hereby corrected as shown below:

In the Claims

Column 47, Lines 1-16, Claim 10,
Compound Group A-22

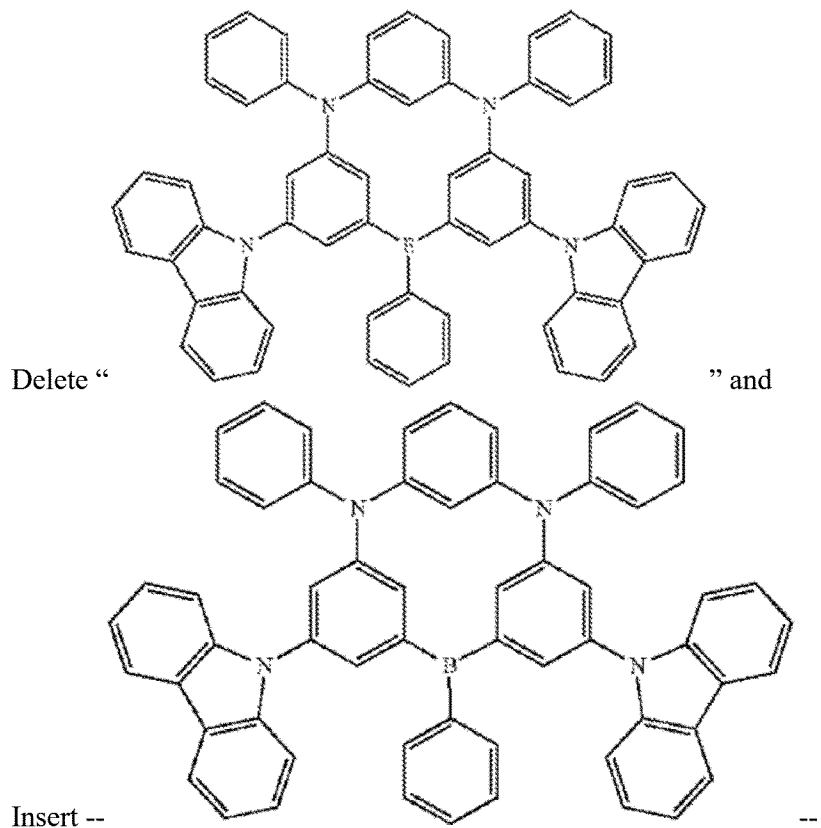

Delete " " and

Insert -- --

Signed and Sealed this
Fifth Day of September, 2023

*Katherine Kelly Vidal*

Katherine Kelly Vidal
*Director of the United States Patent and Trademark Office*

CERTIFICATE OF CORRECTION (continued)
U.S. Pat. No. 11,335,862 B2

Column 47, Lines 36-50, Claim 10,
Compound Group A-24

Delete " 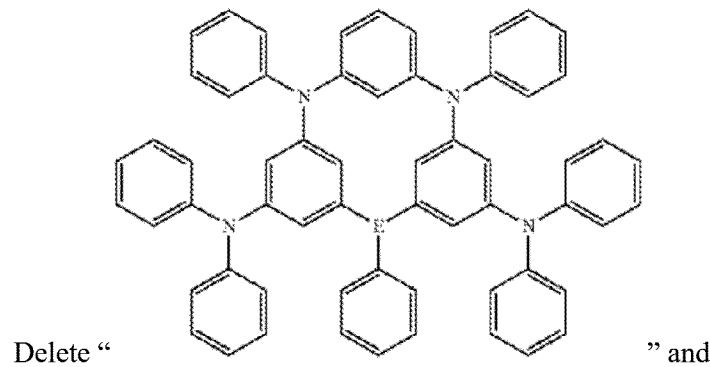 " and

Insert -- 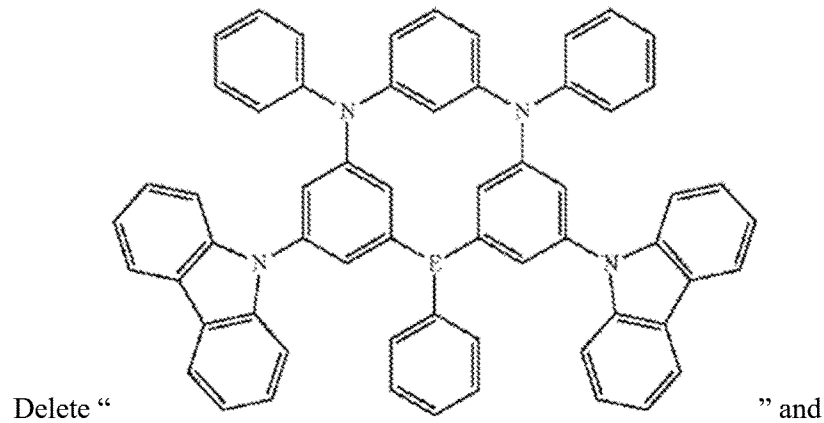 --

Column 56, Lines 21-33, Claim 19,
Compound Group A-22

Delete " " and

CERTIFICATE OF CORRECTION (continued)
U.S. Pat. No. 11,335,862 B2

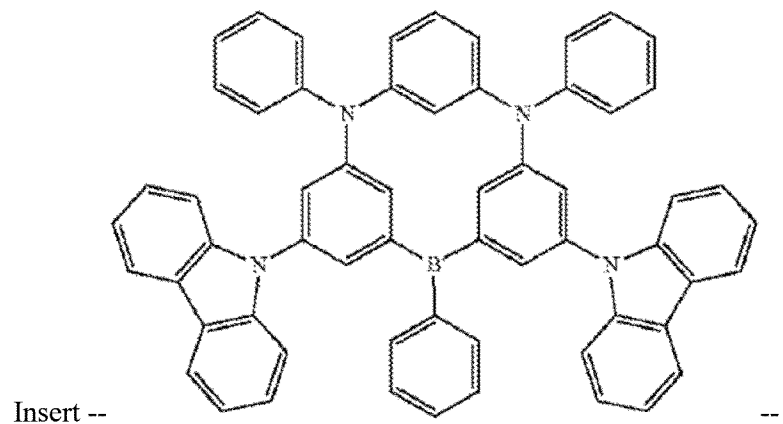

Insert -- --

Column 56, Lines 54-67, Claim 19,
Compound Group A-24

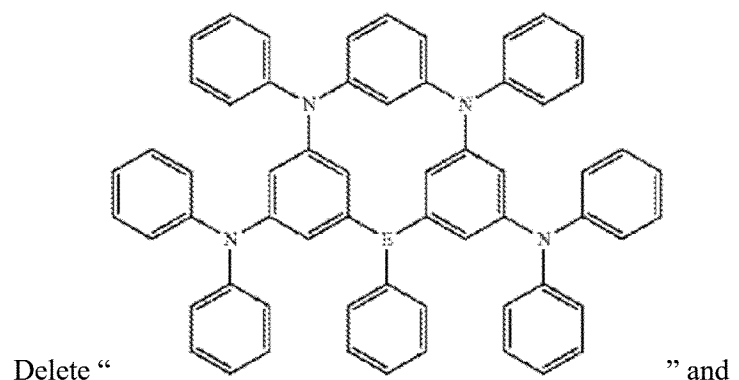

Delete " " and

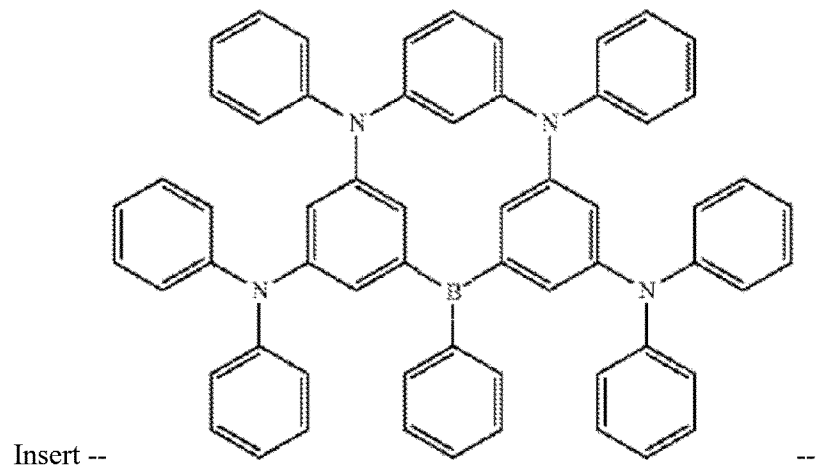

Insert -- --